United States Patent [19]

Shaw et al.

[11] Patent Number: 5,755,744
[45] Date of Patent: May 26, 1998

[54] ELECTRO-CONVULSIVE THERAPY (ECT) SYSTEM WITH ENHANCED SAFETY FEATURES

[75] Inventors: John B. Shaw; Richard A. Sunderland, both of Aloha, Oreg.

[73] Assignee: Mecta Corporation, Lake Oswego, Oreg.

[21] Appl. No.: 934,238

[22] Filed: Sep. 19, 1997

Related U.S. Application Data

[63] Continuation of Ser. No. 562,336, Nov. 24, 1995, abandoned.

[51] Int. Cl.$^6$ ........................................... A61N 1/08
[52] U.S. Cl. ........................................... 607/45; 607/72
[58] Field of Search ........................................... 607/45, 46, 63, 607/72

[56] References Cited

U.S. PATENT DOCUMENTS

| | | | |
|---|---|---|---|
| 2,438,875 | 3/1948 | Offner | 607/45 |
| 4,184,485 | 1/1980 | Agoston | 128/670 |
| 4,363,324 | 12/1982 | Kusserow . | |
| 4,777,952 | 10/1988 | Pavel | 128/419 |
| 4,870,969 | 10/1989 | Swartz | 128/419 |
| 4,873,981 | 10/1989 | Abrams et al. | 128/419 |
| 4,878,498 | 11/1989 | Abrams et al. | 129/419 |
| 4,940,058 | 7/1990 | Taff et al. | 128/653 |
| 5,237,991 | 8/1993 | Baker, Jr. et al. | 607/27 |
| 5,269,302 | 12/1993 | Swartz et al. | 128/419 |
| 5,470,347 | 11/1995 | Swartz et al. | 607/45 |

FOREIGN PATENT DOCUMENTS 2057889  4/1981  United Kingdom .

OTHER PUBLICATIONS

Swartz, Conrad M. and Abrams, Richard, *ECT Instruction Manual*, pp. 6–27; 40–51; 59–70 and Table 2, Jan., 1994.

Thymatron DGx, 3 pages, 1994.

Mecta Domestic Service Manual. Rev. 9900–0010, pp. 13–41., 1985.

Mecta Domestic Instruction Manual. Rev. 9900–1008, pp. 1–13; 28–55; 60–74., 1985.

Strong, Peter, *Biophysical Measurements*, pp. 104–105, 1970.

Hewlett Packard Defibrillator, Model 43130A–1, pp. 2–4., 1985–1986.

UFI Model 1020 PPG, 2 pages, Jul. 1985.

Physio–Control Corporation, Lifepak 9P, pp. 1–16 and 5–41.

(List continued on next page.)

*Primary Examiner*—Jeffrey R. Jastrzab
*Attorney, Agent, or Firm*—Marger, Johnson, McCollom & Stolowitz, P.C.

[57] ABSTRACT

An electro-convulsive therapy (ECT) system includes both hardware and software safety detectors and monitors, including a pulse generator that generates a pulse train of a plurality of pulses with parameters specified by the user. The safety monitors monitor these user-specified parameters as well as other important pulse parameters both during treatment of a patient and prior to treatment in order to ensure that the system is operating according to specification and, therefore, will not injure the patient. The pulse generator is responsive to the safety monitors in that if any of the safety detectors detect a parameter that is out of tolerance, the safety monitor disables the pulse generator so that no further pulses are delivered to the patient. The safety detectors detect plurality of pulse characteristics including pulse width, frequency, voltage, current, treatment duration, as well as energy. In addition to these real time safety checks, the system includes a pre-treatment arming routine that applies a pre-treatment ECT pulse train to an internal load and monitors these same parameters during this internal test. If all of these parameters are within tolerance, the system moves to an armed state in which the user can proceed to apply an ECT treatment pulse train. If any one of these safety checks fails, however, the system does not arm and, therefore, prohibits treatment.

15 Claims, 16 Drawing Sheets

OTHER PUBLICATIONS

Widrow, Bernard and Stearns, Samuel D., *Adaptive Signal Processing*, Chapter 6, pp. 99–101, 1985.

Physio–Control Corporation, Lifepak 9P, pp. 1–16 and 5–41, (1993).

Microcomputers in Safety Technique, by H. Holscher and J. Rader, pp. 3–7, 8;3–11, 12;4–5.6; 4–15, 16 and 7–5, 6 (1984);.

Deutsche Elektrotechnische Kommission Prestandard DIN V VDE 0801 Principles for Computers in Safety–Related Systems (2d Proof English Translation) pp. 33, 37–39, 68, 69, 78 and 106 (Oct. 1991).

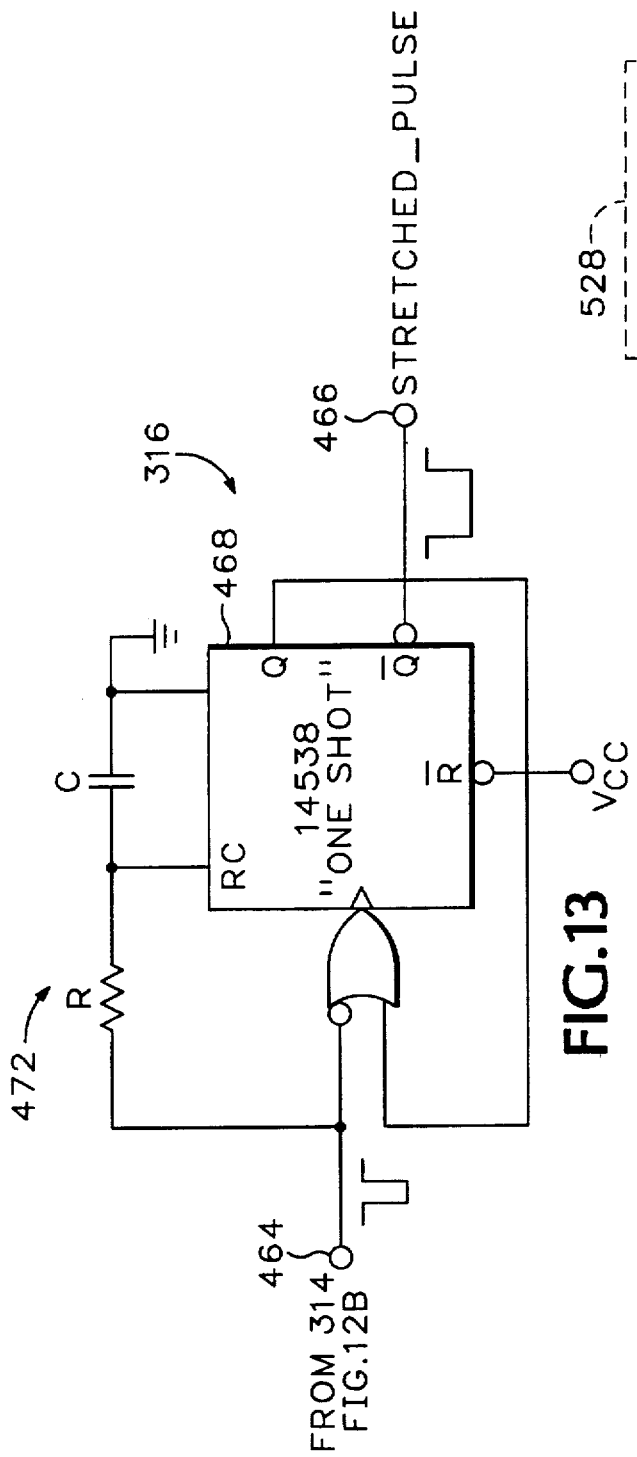
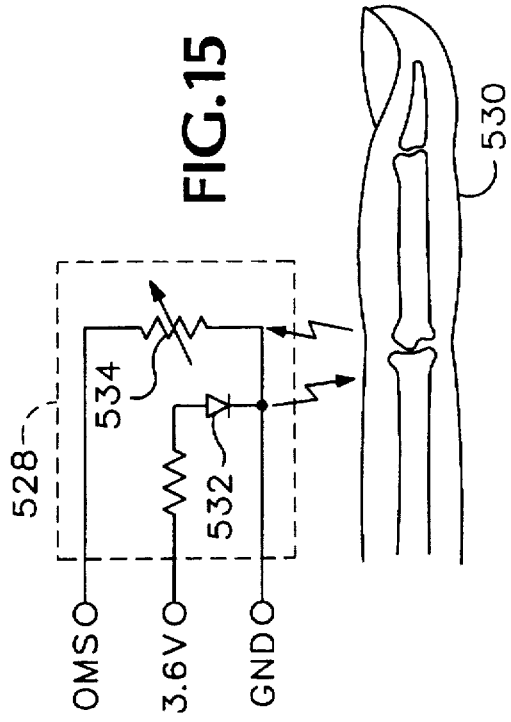
FIG.13
FIG.15

ELECTRO-CONVULSIVE THERAPY (ECT) SYSTEM WITH ENHANCED SAFETY FEATURES

This is a continuation of application Ser. No. 08/562,336, filed Nov. 24, 1995 now abandoned.

BACKGROUND OF THE INVENTION

In the early portions of the Twentieth Century, there was a great feeling of desperation within the mental health community. Mental health hospitals were filled with thousands upon thousands of severely and chronically ill individuals, predominantly schizophrenic, for whom there were no viable means of therapy. Acting upon some erroneous data which indicated that there appeared to be an antagonism between schizophrenia and epilepsy, the Hungarian neuropsychiatrist, Meduna, attempted to induce seizures in schizophrenics by injecting oil of camphor intramuscularly. Within a year following his initial successful report of such use in the management of schizophrenia in 1935, news of the use of induced seizures for such a purpose spread around the world. A long, hoped for breakthrough had now occurred.

Producing seizures with the use of camphor, however, was by no means a pleasant or even reliable task. Even though camphor was almost immediately replaced by a pure pharmacologic preparation, pentylenetetrazol (or Metrazol), the use of this technique was still hampered by the presence of painful myoclonic contractions occurring prior to seizure onset. Occasionally, difficulty in inducing seizures at all, lack of predictability when the seizure would occur, and the possible presence of prolonged and recurrent seizure activity. Still, the therapeutic benefits of pharmacoconvulsive therapy, as it was called, clearly appeared to outweigh the difficulties.

Among those who were impressed by the early successes of pentylenetetrazolinduced seizures was the Italian neuropsychiatrist, Cerletti, who was at that time heavily involved in epilepsy research, using electrical stimulation to produce seizures in animals. Believing that therapeutic seizures in humans could be produced more easily and in a manner more tolerable to patients, Cerletti and his colleague, Bini, attempted to use their techniques clinically in 1937. The success of their initial report of such use in 1938 was heralded by psychiatrists as a significant improvement in the form of convulsive technique, and within one or two years had spread into clinical practice on a worldwide basis.

During the 1940's and throughout much of the 1950's electro-convulsive therapy (ECT) was a mainstay of psychiatric management of severe mental health disorders. As with any powerful new form of treatment, it was used on an extremely widespread basis. Over the course of this period of its use, it became clear that while ECT was occasionally useful at treating schizophrenia, its effects were even more beneficial in the management of severe affective disorders, particularly major depressive episodes. With the development of effective psychotropic alternatives for treating schizophrenia and affective disorders, beginning in the mid-1950's, the use of ECT began to decline.

At present, ECT is used sparingly. It is estimated that in the U.S., only three to five percent of psychiatric in-patients receive this treatment modally, and that between 30,000 to 100,000 patients per year are involved. Many psychiatrists believe that the decline in ECT utilization has now reached a turning point, in that there now appears to be a growing acceptance of its continual clinical role with respect to available therapeutic alternatives. Until the day comes when more effective and less toxic drugs or procedures become available, it is likely that ECT will continue to be used.

In their initial use of ECT, Cerletti and Bini were quite uncertain and apprehensive as to the proper means of stimulus dosage. Consequently, the first ECT machine was a rather complicated, ornate-appearing device, with numerous dials, buttons and controls. The type of electrical signal utilized by Cerletti and Bini was the sine wave, which is what is present in electrical sockets in homes and offices. As one would expect, this type of stimulus waveform was utilized because of its ready availability. If one looks on an oscilloscope, the household sine wave represents an undulating pattern of voltage or current, varying with time and repeating fifty to sixty times a second depending on the country.

Following the initial reports of actual stimulus parameters required to induce a seizure, in the absence of data pointing toward any direct electrical damage upon the organisms from such dosage levels, there was a drift among ECT device manufacturers to simpler and simpler devices. In some settings, this resulted in the use of stimulus electrodes which were plugged directly into a wall socket. In most cases, however, at least the presence of an "ON" button, along with a control for increasing or decreasing voltage or current, was present.

The early discovery that induced seizures were associated with confusion and amnesia, however, led researchers to try and experiment with the nature of electrical stimulus, under the assumption that more energy-efficient stimuli might have less detrimental side effects. By the mid- 1940's, Lieberson and colleagues had found that an interrupted stimulus pattern, consisting of brief, rapidly rising and falling pulses of electricity, separated by longer periods of electrical inactivity, offered the promise of producing seizures on a more efficient basis with seemingly less confusion and amnesia. Unfortunately, most practicing psychiatrists were either not aware of or were not impressed by this data. There was a feeling that the confusion and amnesia were either unimportant or perhaps even useful therapeutically. In addition, there were severe methodological problems with their early studies, as there were almost universally with investigations taking place during this time period. Accordingly, the use of the sine wave stimulus, at least in the U.S., continued to be extremely widespread into the 1970's.

In the mid-1970's the late psychiatrist and prominent ECT researcher, Paul Blachley, decided that, given the degree of concern over memory deficits which had arisen during the ongoing controversy over unilaterally, nondominant versus bilateral electrode placement, an attempt should once more be made to offer an option of brief-pulse stimulus waveform with ECT devices. In addition, Blachley felt that this "optimal" device should also incorporate the capacity of monitoring both EEG and ECG; and should offer the user a clear means to test the safety of the electrical circuit before delivering the stimulus; and finally, that it should be able to offer the ability to allow careful titration to individuals' seizure thresholds. After design and testing efforts, this device, which was known as the MECTA (Monitored Electro-Convulsive Therapy Apparatus) went on the market in 1977, and readily grew in popularity over the following years.

Based on a number of developments in the research literature, and comments and suggestions by psychiatrists using ECT devices, a new generation of MECTA devices was placed on the market. This new generation included the SR and JR models manufactured and sold by MECTA Corporation, of Lake Oswego, Oreg. Although this new generation of ECT devices was an improvement over existing devices in terms of safety, effectiveness and ease of use, there were still additional improvements to be made in all of these areas.

The SR and JR models include two safety features. The first feature uses a "self-test." Despite its name, the "self test" does not test the device itself but instead measures the static patient impedance prior to application of an ECT stimulus. The clinician instigates this test by pushing a self-test button on the device after the ECT electrodes are positioned on the patient. The ECT device then measures the impedance running from the ECT device through an ECT electrode, the patient, the other ECT electrode, and back to the device. During the self-test, the device passes a minute current through the circuit. These models measure the impedance by measuring the voltage produced across the circuit and dividing that measured voltage by an assumed current level. The calculated static impedance is then compared to a predetermined range of static impedances. If the calculated static impedance is within that range, the self-test passes. Otherwise, the self-test fails.

If the static patient impedance is outside the acceptable range, the device inhibits delivery of an ECT stimulus unless an "impedance override" button is pressed. The impedance override button allows clinicians to bypass the self-test failure and engage a stimulus delivery sequence where the extreme static impedance value is due to a peculiar patient's characteristics.

The SR and JR models from MECTA also allow the clinician or other technician to verify that the device is operating within their specified tolerances. This is accomplished by connecting the stimulus output of the device to an external resistor substitution box, i.e., a "dummy" load. A stimulus sequence can then be applied to the dummy load and the resulting signal's characteristics can be measured with the use of an external oscilloscope whose leads are applied across the resistor dummy load. The clinician or technician can then compare the measured signal characteristics as displayed on the oscilloscope with the parameter settings specified by the dial settings on the device. In this way, the frequency, pulse width, duration and energy specifications can be verified. If the device turns out to be out of range or out of specification, the device can then be returned to the manufacturer for repair or recalibration.

Although the self-test and the calibration test are useful, they do not go far enough. The main problem with both of these tests is that they are conducted prior to the ECT treatment sequence and not during the treatment itself. Thus, if one or more of the parameters (current, voltage, pulse width, frequency or duration) were to drift out of range during an actual treatment, this condition would not be detected until the next calibration test. Moreover, the self-test checks only a single parameter, i.e., static impedance, and none of the other parameters which determine the amount of energy actually delivered to the patient.

The MECTA SR and JR devices do display an estimated energy delivered to the patient during treatment. This energy, however, is an estimate based on several assumed parameter values. As is known in the art, energy is a function of voltage, impedance, and time or duration. In the MECTA devices, only the voltage and impedance are measured and the time or duration is assumed based upon the duration setting on the front panel. Thus, if the actual duration of the applied ECT treatment sequence is different than that specified on the front panel, the estimated energy will not equal the actual delivered energy. As a result, the clinician can be misled as to the actual delivered energy.

Accordingly, a need remains for improved parameter monitoring both prior to and during ECT treatment.

SUMMARY OF THE INVENTION

It is, therefore, an object of the invention to improve the safety and reliability of ECT devices.

Another object of the invention is to automate the safety test procedure.

A further object of the invention is to improve the quality of measured patient monitoring signals.

A yet further object of the invention is to provide an improved method and apparatus for monitoring seizure activity.

The invention is an electro-convulsive therapy (ECT) system with advanced safety features. The system includes a means for applying a train of ECT treatment pulses to a patient, a plurality of pulse train parameter detectors that each detect a respective pulse train parameter, and a corresponding plurality of pulse train parameter monitors that disable the applying means if the detected pulse train parameter falls outside of a predetermined range of acceptable values. The monitors operate on a pulse-by-pulse basis and, therefore, provide added safety by terminating a treatment if any of the measured parameters are outside their specified tolerances. This ensures that a safe and effective treatment is applied to the patients in the event a component or circuit fails or drifts out of calibration prior to or during treatment.

The system monitors all of the relevant pulse train signal parameters: voltage, current, pulse width, frequency, pulse train duration, and energy. None of these parameters are assumed, but instead are actually measured. In addition, several of the parameters are measured both by dedicated hardware as well as redundant software monitoring routines. This redundancy provides an additional level of safety heretofore not found in ECT devices.

In another aspect of the invention, the system includes an internal load to which a pre-treatment ECT pulse train can be applied during an internal test. During this internal test, the system monitors all of the pulse train parameters and disables the applying means if a detected parameter of a pre-treatment pulse train is outside the determined range. This includes voltage, current, pulse width, frequency, pulse train duration and energy, as with the actual ECT treatment pulse train.

In yet another aspect of the invention, a frequency adaptive finite impulse response (FIR) filter is described. The adaptive FIR filter is used to eliminate unwanted line frequency interference from patient monitoring signals (e.g., EEG or ECG). The adaptive FIR filter includes means for calculating an estimated signal having an estimated amplitude, estimated frequency and estimated phase; means for subtracting the estimated signal from a received patient monitoring signal to produce an error signal; and means for modifying the estimated amplitude, estimated frequency, and estimated phase of the estimated signal responsive to the error signal. The estimated amplitude, frequency, and phase are modified according a formula derived further herein. The adaptive filter, unlike prior art adaptive filters, adjusts all three parameters (amplitude, frequency, and phase) responsive to the calculated error signal.

The adaptive filter is implemented using a digital signal processor (DSP) that operates under the control of software executed thereby. An analog-to-digital (A-to-D) converter is interposed between a patient monitoring receiver and the DSP for converting the patient monitoring signals to corresponding digital data at a predetermined sampling rate. The DSP then performs the frequency adaptive FIR filtering thereon. The DSP also performs several rate change routines, more commonly referred to as decimation routines to decimate the corresponding digital data into display data at several predetermined sampling rates less than the sampling rate of the A-to-D converter. These sampling rates are chosen according to the invention to correspond to the displays in the system. In one case, the rate change routine executed by the DSP converts the corresponding digital data to LCD display data for a liquid crystal display (LCD) having an LCD sampling rate less than the predetermined A-to-D sampling rate. The LCD sampling rate is chosen so that each datum of the LCD display data can be displayed on the LCD itself in a single pixel such that the display rate of the LCD is approximately 25 millimeters per second, which is the standard display rate in the industry. Alternatively, other displays could be used (e.g., EL, CRT, etc.) and the invention adapted to be compatible therewith.

In yet a further aspect of the invention, an optical motion sensor is described. The optical motion sensor includes a light-emitting diode and light detector. The motion detector is mounted on the "nail" side of the patient's knuckle to detect the seizure activity based on the flexing of the knuckle and on the expansion and contraction of the muscle between the knuckle and the motion detector. The expansion and contraction modulates the amount of light received by the light detector, which in the preferred embodiment, is a photoresistor. The photoresistor produces an output signal that is proportional to the intensity of the received light and, therefore, proportional to the seizure activity. These same devices have been used in the past to detect pulse rate. However, in this case, expansion and contraction of the tissue due to blood flow compromises the accuracy of the motion detector. As a result, the optical motion sensor must be mounted on the patient in an area which does not pulsate in response to blood flow. The "nail" side surface of the knuckle is an example of just such an area.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 13 is a schematic diagram of a pulse extender circuit shown in FIG. 12B.

FIG. 15 is a schematic diagram of the optical motion sensor and its use according to the invention.

TABLE OF CONTENTS
I. ORGANIZATION
  A. SYSTEM ARCHITECTURE (FIGS. 1A–1B)
  B. SYSTEM PROCESSOR (FIG. 2)
  C. PATIENT MONITORING SECTION (FIGS. 3A–3B)
  D. ANALOG-TO-DIGITAL CONVERTER SECTION (FIG. 4)
  E. ADAPTIVE FILTER (FIGS. 5–6)
  F. LCD DISPLAY SECTION (FIG. 7)
  G. FRONT PANEL SECTION (FIG. 8)
  H. DIGITAL-TO-ANALOG CONVERTER SECTION (FIGS. 9–10)
  I. SAFETY MONITORING SECTIONS (FIGS. 11A, 11B, 12A, 12B, 13)
II. OPERATION
  A. TEST SEQUENCING (FIG. 14)
  B. OPTICAL MOTION SENSOR (FIG. 15)

DETAILED DESCRIPTION
I. ORGANIZATION

A detailed description of the electro-convulsive therapy (ECT) system is given below. First, an overall description of the system's architecture and organization is provided, followed by a more detailed description of several major components within that architecture.

A. SYSTEM ARCHITECTURE (FIGS. 1A–1B)

Figure 1A:
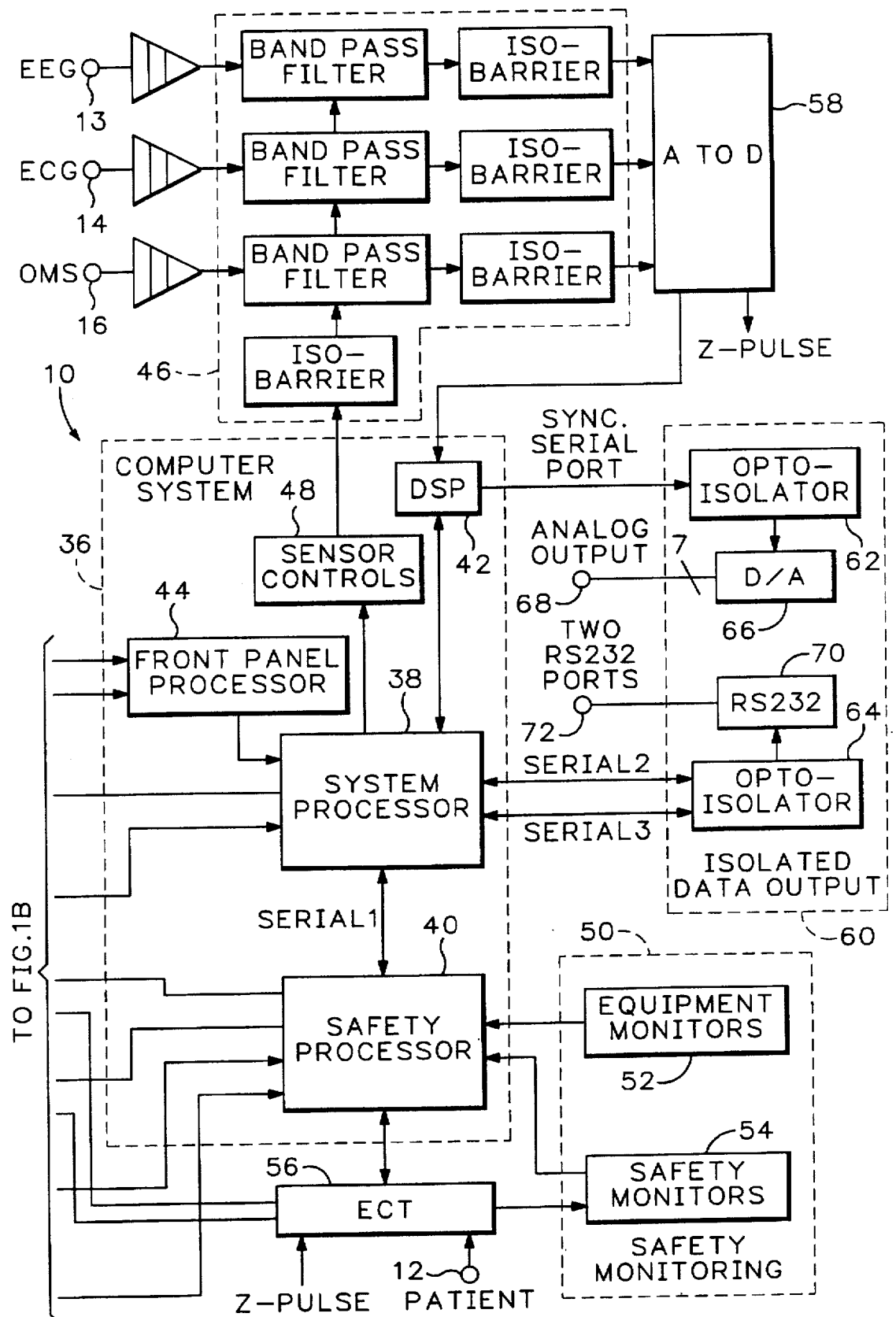
FIGS. 1A and 1B are a block diagram of the ECT system according to the invention.
Figure 1B:
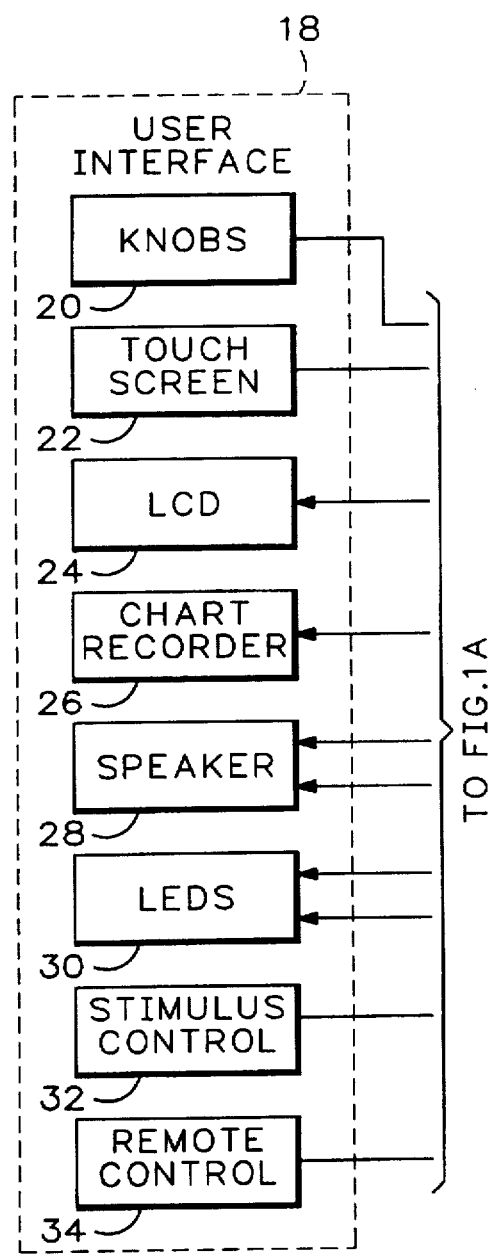

Referring now to FIGS. 1A and 1B, an ECT system is shown generally at 10. Certain common components are not shown for simplicity, for example, the power supplies. The ECT system 10 includes several connections to the patient. The first connection is the ECT stimulus electrodes 12 through which an ECT treatment pulse train is applied to the patient and through which the patient treatment electrode interface impedance is measured. In addition, the system also includes several patient monitoring inputs 13, 14 and 16 that connect to the patient to receive EEG, ECG and/or OMS (optical motion sensor) signals, respectively. The apparatus and method for generating the ECT pulses and monitoring the patient signals is discussed further below.

The system 10 further includes a user interface 18 through which the user, typically a psychiatrist, interacts or interfaces with the system 10. In one embodiment of the user interface, a plurality of knobs 20 are included for setting the parameters that define the ECT pulse train. These parameters include the frequency of the pulse train, the pulse width of each individual pulse in the train, the current level, and the duration of the ECT pulse train.

In another embodiment of the user interface, only a single knob is included to allow the user to set a single stimulus intensity parameter (e.g., energy or charge). All of the pulse train parameters (pulse width, frequency, current, and duration) are then established based on this setting of this single stimulus intensity parameter. The user interface 18 also includes a touch screen 22 which is a touch-sensitive display that allows the user to input commands to the system by touching certain portions of the screen. The system is menu driven so that the user can quickly and efficiently move through the command options. A liquid crystal display (LCD) 24 is provided to display certain information to the user both prior to and during treatment. A chart recorder 26 provides a hard copy output of the patient monitoring signals. The system 10 further includes a speaker 28 that sounds an audible alarm when certain failures occur in the system, which are described further below and, as a safety feature whenever the ECT section is activated. Light-emitting diodes (LEDs) 30 are also provided as indicator lights for the user. A stimulus control section 32 is provided to allow the user to initiate a treatment. As an alternative, a remote control section 34 is provided that allows the user to initiate a treatment while out of reach of the system. The remote control section 34, which works in conjunction with stimulus paddles, disables the (front panel) stimulus control section 32 so that when remote-control-equipped paddles are plugged into the system, a treatment cannot accidentally be initiated from the stimulus control section on the user interface.

At the heart of the ECT system 10 is a computer system 36 which orchestrates the operation of the system. The computer system includes four processors: a system processor 38, a safety processor 40, a digital signal processor 42, and a front panel processor 44. The system processor 38 is coupled to the knobs, touch screen, LCD, and chart recorder of the user interface 18. The knobs 20 and touch screen 22 are coupled to the system processor 38 via the front panel processor 44 that emulates a standard keyboard interface. Thus, the system processor communicates to and from the knobs and touch screen as it would a standard IBM keyboard. This approach was useful during development of the system because the knobs and touch screen could then be replaced by a keyboard to provide input to the system.

The system processor 38 is coupled directly to both the LCD 24 and the chart recorder 26 to provide display data directly thereto. As will be described further below, the display data is generated by the DSP 42, which decimates the digitized patient monitoring signals to a sampling rate that is compatible with the two displays (i.e., LCD and chart recorder).

The system processor 38 is also coupled to a patient monitoring section 46 through a sensor control block 48 and an iso-barrier. The sensor control block 48 includes logic that decodes signals received from the system processor 38 and configures the patient monitoring section 46 into various modes responsive thereto. These modes include the normal operational mode in which the patient monitoring signals are received from the patient and test modes wherein the accuracy of the section is tested. The patient monitoring section 46 is described further below in subsection I(C).

The computer system 36 also includes a safety processor 40. The safety processor is primarily responsible for coordinating the various safety tests and checks that are performed on and by the ECT system. The safety processor 40 is coupled to the system processor 38 via a serial interface (SERIAL 1). The safety processor 40 is also coupled to a safety monitoring section 50 which includes equipment monitors 52 and safety monitors 54. These monitors 52 and 54 monitor both the equipment as well as the stimulus to determine whether or not the system is performing within specification and, if not, to disable any further treatments.

The safety monitor 54 is further coupled to an ECT block 56 which generates the ECT pulse train responsive to the safety processor 40. The ECT block 56 is directly coupled to the timing circuits of an A-to-D converter 58 to receive a Z_PULSE signal that is generated during every sample taken by the A-to-D converter 58. The Z_PULSE is used by the impedance-measuring portion of the ECT block 56 to measure patient impedance, as described further below. The A-to-D converter 58 digitizes the patient monitoring signals received at inputs 13, 14 and 16 (i.e., EEG, ECG and OMS). This digitized data is then operated on by the DSP 42 to filter out unwanted power line frequency interference by the use of a frequency adaptive finite impulse response (FIR) filter as well as decimate the digitized data for display.

Safety processor 40 is directly coupled to speaker 28, LED 30, stimulus control 32 and remote control 34. The safety processor 40 initiates an ECT treatment sequence, under certain predetermined conditions, responsive to inputs received from either stimulus control 32 or remote control 34. Both the ECT block 56 and the safety processor also actuate either the speaker or the LEDs if certain conditions exist, e.g., internal self-test failed. This provides redundant fault and "arming status" indications for safety purposes.

The final section of the system 10 is the isolated data output section 60. This section is coupled to the computer system 36 via three serial ports: a synchronous serial port (SYNC SERIAL PORT) and two asynchronous serial ports (SERIAL 2, SERIAL 3). The computer system 36 is isolated from the isolated data output section 60 by opto-isolator blocks 62 and 64. The opto-isolator block 62 is interposed between the DSP 42 and a digital-to-analog converter 66. The DSP 42 transmits the digitized patient monitoring signals to the digital-to-analog converter in order that those signals may be observed by external equipment coupled to analog outputs 68. Similarly, the system processor 38 communicates the LCD and chart recorder display data via opto-isolator block 64 to an RS-232 interface block 70, which provides two RS-232 serial output ports 72 to enable this data to be printed, displayed, or stored by an external peripheral such as a printer or computer. The isolation barriers here protect the patient and the operator from shock hazards should electrical faults occur in the external equipment.

B. SYSTEM PROCESSOR (FIG. 2)

Figure 2:
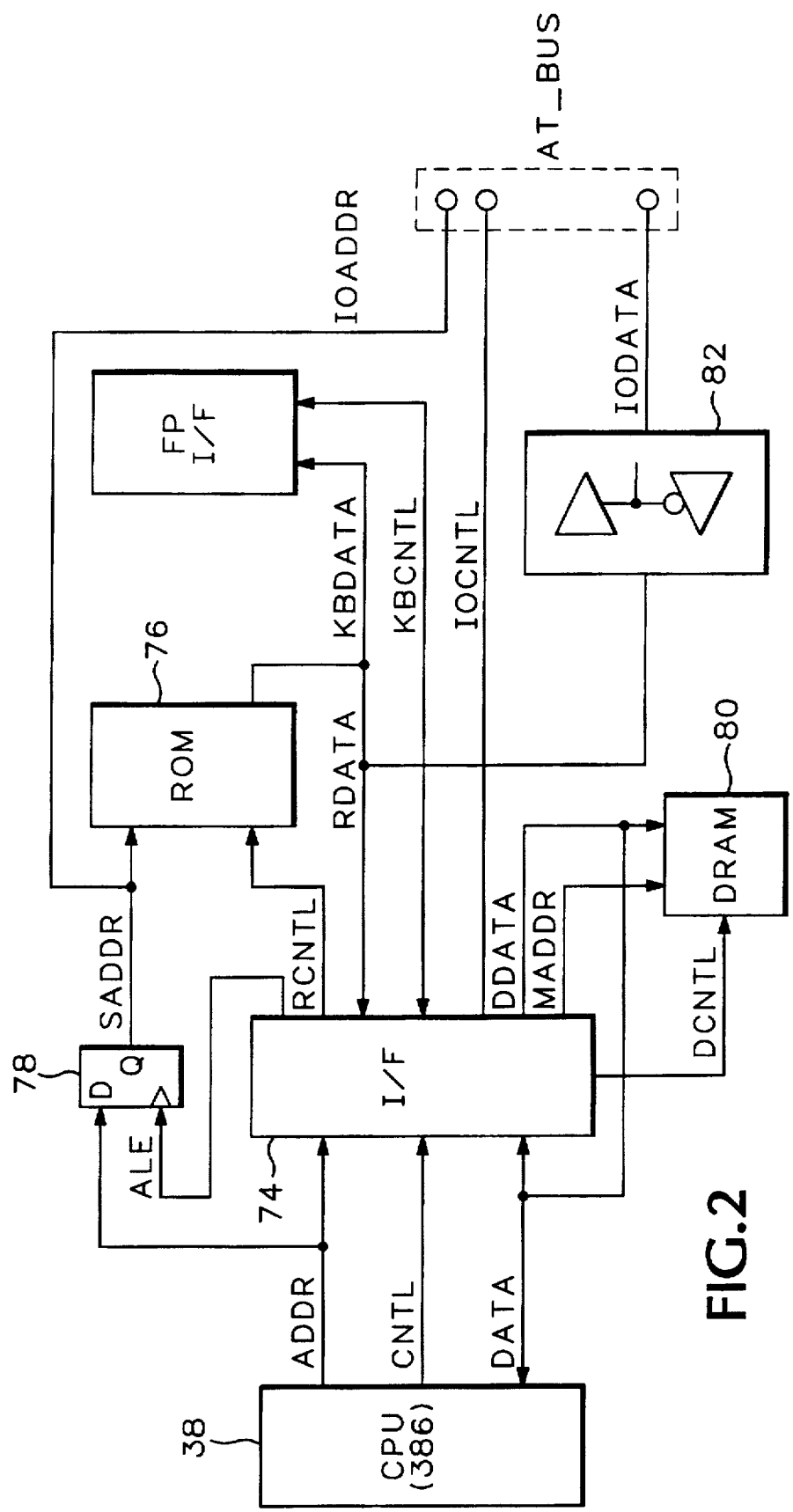
FIG. 2 is a block diagram of the system processor of the system shown in FIG. 1.

Referring now to FIG. 2, a more detailed schematic of the system processor is shown. The system processor in the preferred embodiments is an 80386(386) microprocessor manufactured by either Intel or Advanced Micro Devices. The organization shown in FIG. 2 is a typical organization employed in, for example, personal computers, in order to take advantage of the numerous components that have been designed for 386-based systems. The 386 microprocessor includes an address bus ADDR, a data bus DATA, and a control bus CNTL. These buses are coupled directly to an interface chip 74 which generates the signals necessary for the 386 to communicate with the other components in the system. The interface chip 74 can either be a standard off-the-shelf part that is sold by a variety of manufacturers such as Chips and Technology or, alternatively, can be an application specific integrated circuit (ASIC), which can then be manufactured by any number of semiconductor companies.

The 386 microprocessor 38 is coupled to a read-only memory (ROM) 76, which includes the object code of the 386 microprocessor. The ROM 76 provides a 16-bit word to the 386 responsive to a chip select signal RCNTL generated by interface chip 74 responsive to a read within a predefined address range being decoded thereby. The particular address location within the ROM is specified by an address SADDR that is latched in latch 78 responsive to a latch signal ALE generated by the interface chip 74.

The interface chip 74 also provides an interface between the 386 microprocessor and dynamic random access memory (DRAM) 80. As is known in the art, DRAM has a unique interface that requires both a row and a column address multiplexed over a common address bus (MADDR) as well as certain control signals to be provided in a predetermined sequence. The interface chip 74 provides that multiplexed address as well as the appropriate control signals responsive to a valid read or write by the 386 within a predefined DRAM address range. The logic within the interface chip 74 required to perform this interface is well known and is not described further herein.

As described above, the system processor 38 communicates with the knobs and touch screen via a simulated keyboard interface. The interface chip 74 generates the control signals on keyboard control bus KBCNTL necessary to communicate with the front panel processor 44.

The computer system 36 communicates with several of the other blocks and components via the industry standard AT bus. The AT bus is comprised of address bus IOADDR, data bus IODATA, and control bus IOCNTL. The AT bus was chosen because of its simplicity since the data latency and throughput of the AT bus is adequate for this application. This also facilitated a back plane architecture of the system that allowed different portions to be located on separate printed circuit boards that could be selectively removed from the system in the event of a failure of a particular component or section. The interface chip 74 along with the bidirectional data buffers 82 and latch 78 provide the signals for the AT bus interface. Because this interface is so well known in the art, the logic necessary to support the AT bus is not discussed further herein.

C. PATIENT MONITORING SECTION (FIG. 3)

Figure 3A:
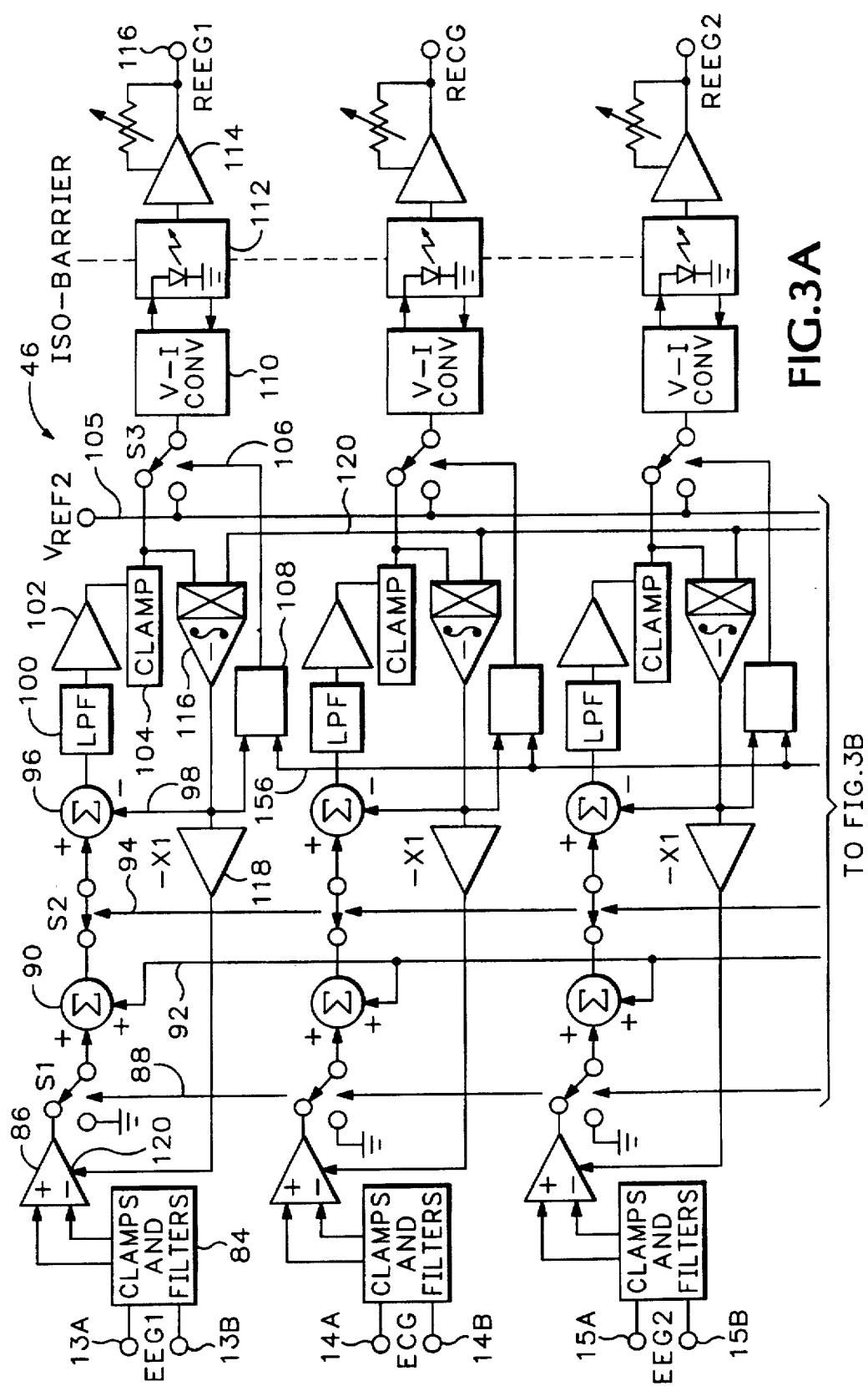
FIGS. 3A and 3B are block diagrams of the patient monitoring section of the system shown in FIG. 1.
Figure 3B:
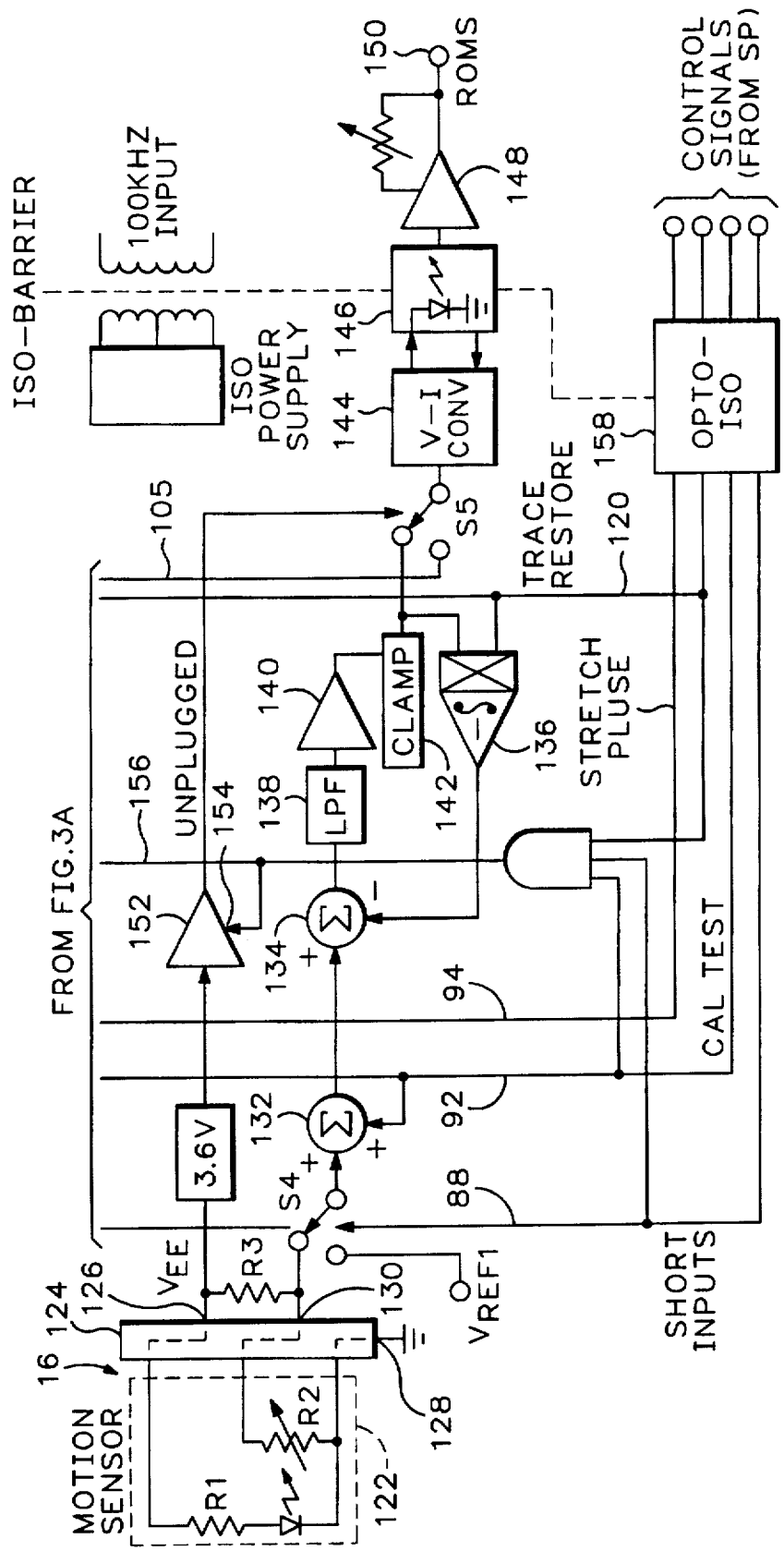

Referring now to FIGS. 3A and 3B, a detailed block diagram of the patient monitoring section is shown generally at 46. FIG. 3A includes the circuitry for three patient monitoring signals (EEG1, EEG2, and ECG) while FIG. 3B includes the circuitry for the optical motion sensor signal (OMS). The circuitry for each of the three patient monitoring signals shown in FIG. 3A is similar in function, and therefore only one will be described in detail.

The patient inputs are comprised of leads 13A and 13B, which can be applied to a patient by (monitoring) electrodes. The patient monitoring signal EEG1 is then received across these two leads. The patient monitoring signal is then clamped and filtered by clamp and filter block 84, which is coupled to an input amplifier 86. The clamped filter block limits the input range of the patient monitoring signal as well as performs some preliminary filtering (to reduce interference from RF noise sources in particular) on the signal.

The input amplifier 86 is an instrumentation amplifier which is controlled by a feedback loop described further below. The output of the input amplifier 86 is coupled to a two-position switch S1 whose state is controlled by a test signal SHORT INPUTS appearing on line 88. Switch S1 is further connected to a summing circuit 90, which sums the switch output signal with a signal appearing on line 92. The signal on line 92 is a calibration signal approximately 0.2 mV (for EEG) referenced to input (RTI). This signal is used during the calibration test mode, which is entered by asserting SHORT INPUTS on line 88. Asserting SHORT INPUTS on line 88, causes switch S1 to switch the input of summing circuit 90 to a ground terminal and therefore the output of the summing circuit 90 is the calibration signal (CAL TEST) appearing on line 92 whose value is accurately known to the system. In this way, the system can verify the accuracy of most of the input section by comparing the signal level produced by the input section with the expected signal level of the calibration signal.

The output of the summing circuit 90 is connected to an input of a second switch S2. Switch S2 switches between a floating state wherein the input of summing circuit 96 holds the last voltage it had received from summing circuit 90 prior to S2 opening, and a closed state wherein the output tracks the input patient monitoring signal. Switch S2 is used to decouple the input section from the patient during each pulse of an ECT treatment. Switch S2 is responsive to signal STRETCHED PULSE on line 94, pulsed by the safety processor for each treatment pulse delivered to the patient, but lengthened in duration by the ECT section. The STRETCHED PULSE signal in combination with switch S2 allows the signal channel to ignore treatment pulses, since STRETCHED PULSE begins very slightly before a treatment pulse reaches the patient and continues for enough time after a treatment pulse is finished for input amplifier 86 and the patient monitoring electrodes to restabilize.

The output of switch S2 is coupled to a first input (+) of a summing circuit 96. A second input of summing circuit 96 is connected to line 98, which provides a feedback signal that is subtracted from the output signal of switch S2 by the summing circuit 96. The output of the summing circuit 96 is coupled to a low pass filter (LPF) 100. The output of the low pass filter 100 is connected to an inverting amplifier 102 which, as the name implies, inverts the output of the low pass filter. The output of the inverting amplifier 102, in turn, is clamped by a clamp 104, which limits the input voltage applied to integrator 116 and to V-I converter for 110.

The output of the clamp is connected to a first input of switch S3 while the second input is connected to a reference voltage $V_{REF2}$. The state of switch S3 is controlled by the signal appearing on line 106. This signal switches the switch between the output of the clamp and the reference voltage under one of two conditions. First, where the output voltage of integrator 116 exceeds a predetermined maximum limit, (which occurs when one or both of the inputs 13A or 13B are unhooked from the patient, or when the DC offset of the signal between inputs 13A and 13B is too large for the channel to handle properly) the switch S3 is switched to the reference voltage $V_{REF2}$. This forces the channel output REEG1 to a known level near, but not at, the limit of its dynamic range. No patient signal could produce such a (sustained) output. System processor 38 recognizes this condition as a channel error condition. Second, the switch S3 can be switched to the reference voltage during the module ID test mode when module ID 156 is asserted. Logic circuit 108 is the circuit that asserts the signal on line 106 responsive to either of these two conditions being satisfied. One of ordinary skill in the art can readily design circuit 108 to switch S3 during either of these two conditions. The standard patient monitoring section (module) can have the aforementioned set of four signal channels present (though some channels can be disabled when not purchased as a fully-equipped option). All of these modules will have a specified voltage for $V_{REF2}$. Optional modules with different channel specifications can use a different voltage for $V_{REF2}$. The system processor 38 can distinguish module type by reading the reference voltage.

The output of switch S3 is connected to a voltage-to-current converter 110 that converts the voltage on the output of switch S3 to a current. This current is then fed to a linear opto-isolation circuit 112 that optically isolates the voltage-to-current converter from an optical receiver also included in 112. Though not shown in detail, the linear opto isolator circuit is comprised of an LED and two photosensors, one each of the latter on either side of the iso-barrier. The photosensors are matched to each other in performance and the LED illuminates each. The V-I converter is responsive to the photosensor on the isolated side as well as to the signal from S3 in a manner to provide a stable, linear signal across the iso-barrier. The output of opto-isolator 112 is coupled to an amplifier 114 whose gain adjustment is set to calibrate the channel. The output of 116 of the amplifier 114 is a received patient monitoring signal REEG1. It is this signal that is operated on by the system.

The input section also includes a feedback path that reduces the DC level at the output of the input amplifier 86 depending upon the DC offset of the patient signal. There are two components in the feedback path: an inverting integrator 116 and an inverting amplifier 118. These two components are connected in series and interposed between the output of the clamp 104 and the reference input 120 of the amplifier 86. The integrator and amplifier remove any long-term drift offset from the patient monitoring signal presented to S3. In ordinary instrumentation amplifier circuits, the reference input would be connected to a fixed voltage, and the maximum gain useable from the amplifier is limited to a value determined by the DC offset that must be tolerated between its inputs, and the output voltage at which the amplifier saturates. By making the amplifier's reference input responsive in a subtractive manner to the DC offset of the patient signal, the usable gain of the amplifier can be nearly doubled yet not saturated. By doubling the gain of the first stage in a signal channel, those familiar with the art know that if that first stage has very low internally-generated noise, that the overall channel noise for a fixed overall channel gain will be improved.

The output of the integrator 116 is connected to line 98 and to the logic circuit 108. Thus, the output signal from the integrator is subtracted from the signal received at the first input of the summing circuit 96, i.e., the patient monitoring signal. The feedback path produces a high pass filter. In conjunction with LPF 100, the total circuit comprises a bandpass filter as shown in FIGS. 1A–1B.

The integrator 116 further includes a second input that is connected to line 120 for receiving a TRACE RESTORE signal. The TRACE RESTORE signal acts to raise the frequency of the high pass filtering, and allows the system processor to rapidly center displayed traces that have drifted outside a displayable range. The system uses this signal to restore the patient monitoring signal to the center of the display range under certain circumstances, for example, if the patient signal is saturated for more than one second.

The input circuitry for the other two patient monitoring signals is substantially identical and therefore not described further. Note, however, that the patient monitoring signals (EEG1, ECG, and EEG2) are merely illustrative and are not limited to those shown. Moreover, the number of signals monitored is not limited to the number shown. Finally, those skilled in the art will be familiar with methods to add a driven reference output responsive to the common mode content of inputs 13A and 13B, or 15A and 15B, or 14A and 14B, to be connected to the patient to reduce common mode signal errors. While beneficial, such a scheme is not required for satisfactory operation.

FIG. 3B shows the input section for an optical motion sensor 122 (which produces a patient monitoring signal OMS shown in FIG. 1A). The optical motion sensor 122 uses a photoelectric technique to detect seizure activity in the patient. Standard pulse sensors, such as provided by UFI of Morro Bay, Calif. can be used to detect this motion. Pulse sensors have been used in the past to detect blood flow by placing the pulse sensor on the underside of a patient's digit, such as their index finger or toe. According to the invention, however, the pulse sensor is placed on the top (i.e., "nail") side of the patient's finger or toe proximate to the joint so that the motion detector detects movement of the joint due to flexing during seizures, while not detecting very much movement due to blood flow.

The motion sensor is coupled to the input section via a connector 124. The connector includes three terminals, two for providing power and ground and one for receiving the signal (OMS) from the motion sensor. The input section provides a 3.6 volt supply voltage $V_{EE}$ over pin 126, ground via pin 128, and receives the motion sensor signal over pin 130. The motion sensor produces an output voltage by the voltage divider action of resistor R3 and photoresistor R2. As the resistance of R2 is modulated by flexing of the patient's knuckle, the voltage of 130 also varies. This signal voltage is provided to one of the inputs of switch S4. Switch S4, like switch S1 described above, is a two-position switch that switches between the input patient monitoring signal and a known reference voltage, in this case, $V_{REF1}$. The output of switch S4 is connected to summing circuit 132 which sums the input signal from the motion sensor with the calibration signal CAL TEST on line 92. The output of summing circuit 132 is provided to a summing circuit 134 along with the output signal of an inverting integrator 136, which along with low pass filter 138, amplifier 140, and clamp 142, form a bandpass filter, as in the other circuits described above. The integrator 136 also includes two inputs: one connected to the output of clamp 142 and the other connected to line 120 to receive the TRACE RESTORE signal.

The output of clamp 142 is connected to a first input of a two-position switch S5, the second input being connected to line 105 to receive the reference voltage $V_{REF2}$. The output of switch S5 is connected to a voltage to current converter 144 that is further coupled to a linear opto-isolator 146, which drives an amplifier 148. The output 150 of amplifier 148 is a received optical motion sensor signal ROMS on output 150. The V-I converter 144 and linear opto-isolator 146 operate in a manner identical to their counter parts 110 and 112 in FIG. 3A.

The input section for the optical motion sensor also includes a current sense amplifier 152. The current sense amplifier 152 detects the amount of current provided by the 3.6 volt supply and switches the state of switch S5 from the output of clamp 142 to the reference voltage $V_{REF2}$ if the detected current is less than a predetermined amount. This condition corresponds to having the motion sensor unplugged. Thus, if the system detects at the output 150, a DC signal level proportionate to reference voltage $V_{REF2}$, the system can indicate that the motion sensor is unplugged. The current sense amplifier 152 also includes an override input 154 that is connected to line 156 which causes the output of the current sense amplifier to switch S5 to the reference voltage $V_{REF2}$ when the signal on line 156 is asserted. The signal on line 156 is asserted when a module ID test function is commanded, as for FIG. 3A, when TRACE RESTORE, CAL TEST, and SHORT INPUTS are all asserted.

These signals and STRETCHED PULSE are provided to the input section from the system processor via an opto-isolator block 158.

D. ANALOG-TO-DIGITAL CONVERTER SECTION (FIG. 4)

Figure 4:
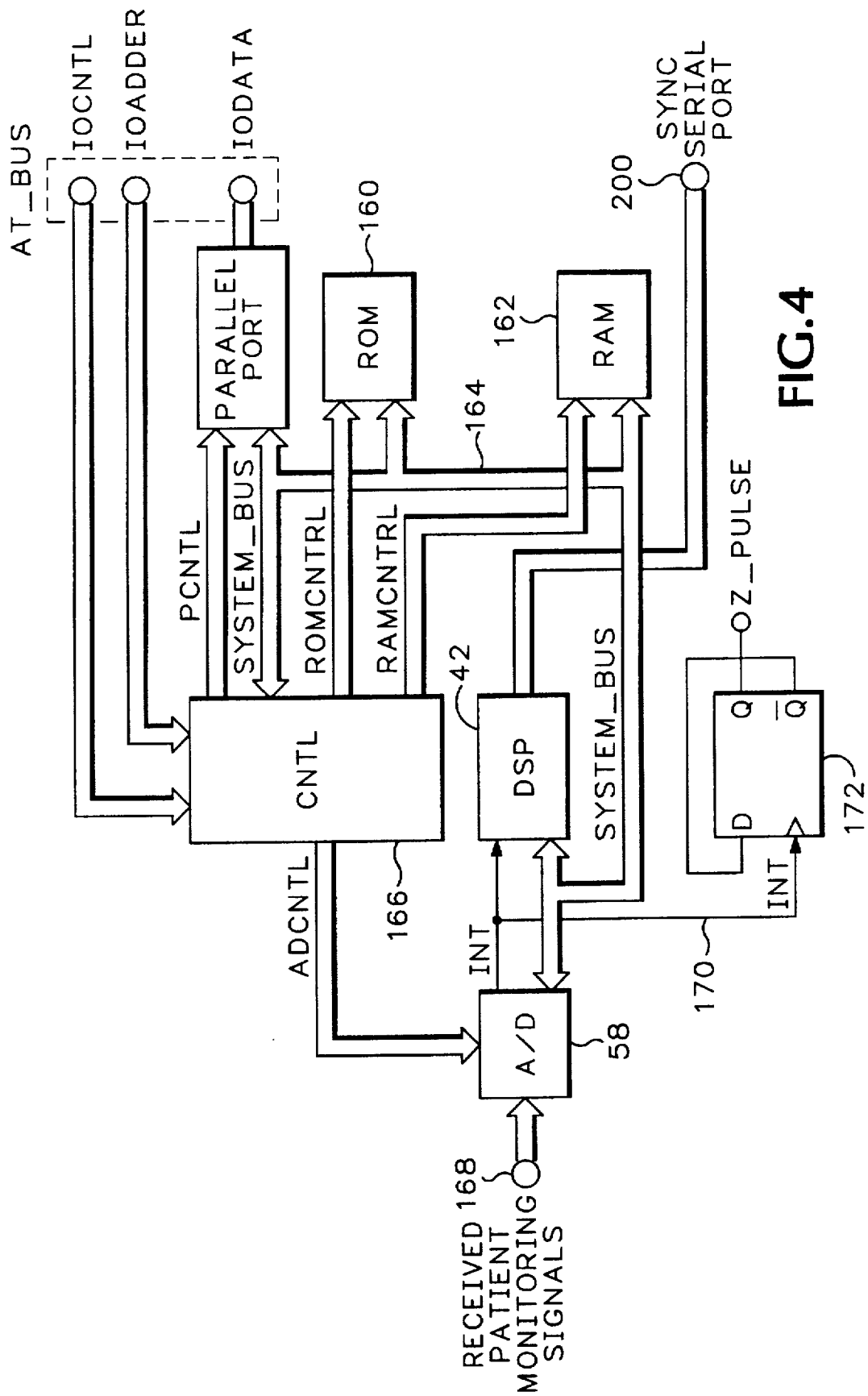
FIG. 4 is a block diagram of the analog-to-digital converter section of the system shown in FIG. 1.

Referring now to FIG. 4, a more detailed block diagram of the A-to-D converter 58 and digital signal processor 42 is shown. The digital signal processor 42 performs two primary functions. First, the digital signal processor filters the incoming patient monitoring signals to remove unwanted line frequency interference. The DSP 42 accomplishes this through the use of a frequency adaptive FIR filter. The second primary function of the DSP is to change the data rate from that produced by the A-to-D converter 58 to those rates required by the various displays in the system. Each of these functions will be described now below.

The digital signal processor is, as its name implies, a processor. Accordingly, it operates under control of a program stored in a read only memory 160. In addition, the DSP 42 uses a local RAM 162 for local read/write storage. The DSP is coupled to these memories 160, 162 over SYSTEM BUS 164, which includes address, data and control signals. The system bus is also connected to the A-to-D converter 58, which allows the DSP to interrogate the A-to-D and read the digitized patient monitoring data therefrom. The SYSTEM BUS 164 is also connected to a control logic block 166 that decodes the address and control signals on the system bus and enables the ROM or RAM accordingly over their respective buses (ROMCNTRL, RAMCNTRL). The control block 166 also provides control signals ADCNTL to the A-to-D converter 58 responsive to the system bus to allow the DSP 42 to read the digitized data therefrom. In this system, the ROM, RAM and A-to-D converter are mapped to unique sections of the DSP memory space.

The received patient monitoring signals from the patient monitoring section are provided to the A-to-D converter 58 via input lines 168. These lines carry the above-described patient monitoring signals including EEG, ECG and OMS. The number of these signals can vary between systems depending upon the number of input sections in the patient monitoring section. The A-to-D converter 58, as is known in the art, samples the patient monitoring signals at a predetermined sample rate, which is determined by a clock signal (not shown) provided to the A-to-D converter 58. The A-to-D converter 58 includes an interrupt output that is connected to line 170 upon which an interrupt signal INT is asserted by the converter 58 when the conversion process is complete. This interrupt signal INT is provided to the DSP 42, which produces an interrupt in the DSP. The DSP 42, responsive to this interrupt, executes an interrupt service routine, wherein the DSP reads the several digitized samples from the A-to-D converter 58. This procedure is described further below with reference to FIG. 5. The interrupt line 170 is also connected to a clock input of a D-type flip-flop 172, which is configured as a divide by two circuit with the inverting output IQ connected to the data input (D). The non-inverting output (Q) of the flip-flop 172 is the Z_PULSE described above and shown in FIG. 1 that is used to synchronize with the A-to-D conversion process the patient impedance measurement function of the ECT section. The DSP can also be used to perform desired statistical patient signal analysis.

E. ADAPTIVE FILTER (FIGS. 5–6)

Figure 5:
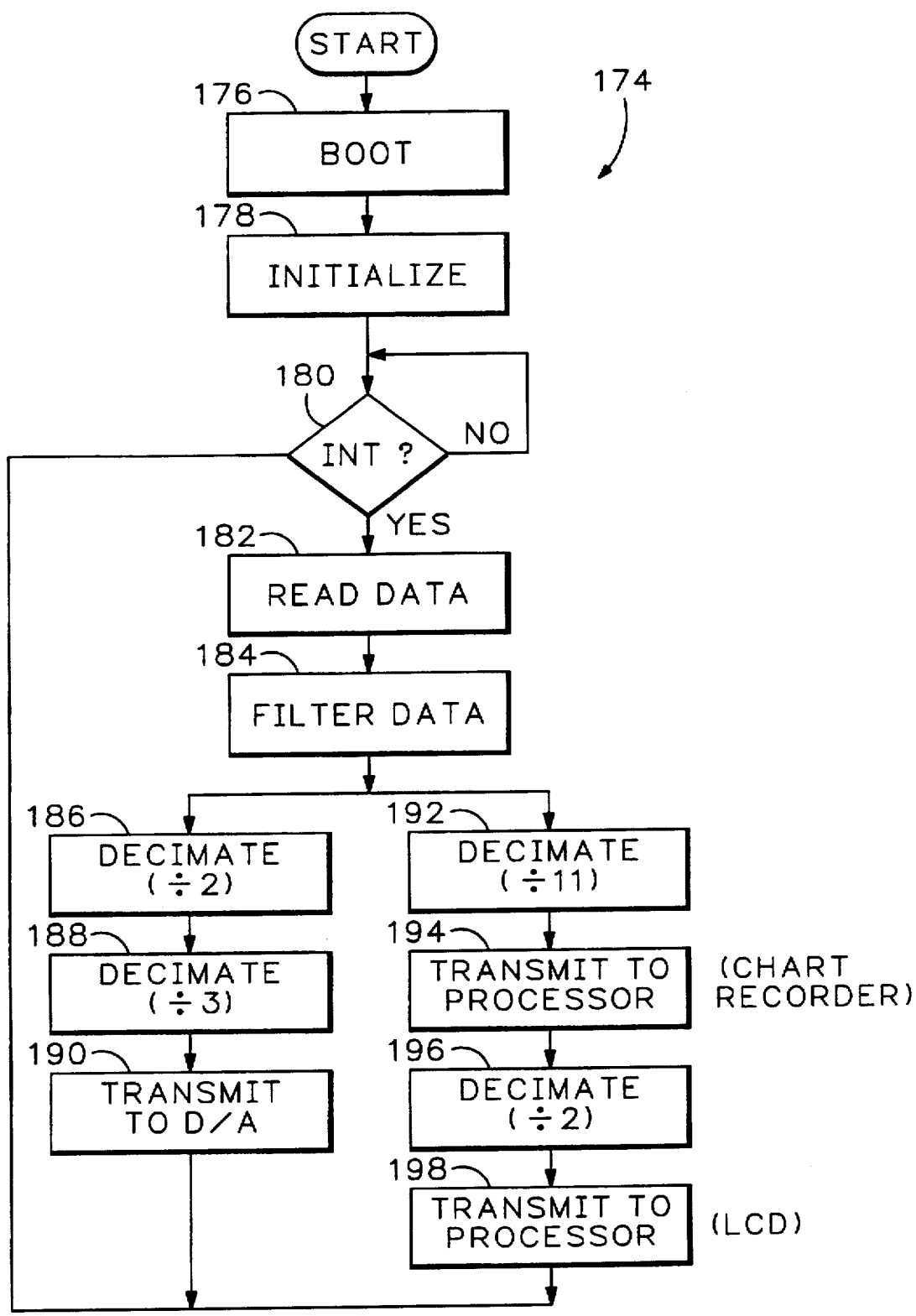
FIG. 5 is a flow chart showing the operation of the digital signal processor (DSP) of the system shown in FIG. 1.

Referring now to FIG. 5, a flow chart for the DSP operation is shown generally at 174. The first step for the DSP upon power-up is to execute a boot routine at 176. This boot routine begins at a fixed address in ROM, usually address zero (OH) and loads up certain boot code into the DSP. Next, in 178, the DSP initializes itself and the A-to-D converter. The content of this step is determined largely by the actual DSP chip and the A-to-D chip used in the implementation.

In step 180, the DSP waits for an interrupt, as described above. If an interrupt is received, the DSP enters its interrupt service routine and reads the digitized data from the A-to-D converter. The number of words read from the A-to-D converter depends upon the number of input channels in the input section as well as the number of available channels in the A-to-D converter. This is performed in step 182.

The DSP then filters the data to remove unwanted line frequency interference. This step is described further below with reference to FIG. 6. The filter according to the invention adapts not only to the amplitude and phase of the digitized data, but also to the frequency. This allows the system to be used in countries which have differing frequencies for their AC power.

The DSP then proceeds to execute several rate change routines, more commonly referred to as decimation routines. These rate change routines change or convert the sampling rate of the data from the sampling rate of the A-to-D converter to a rate required by one of the other sections of the system. Decimation itself is a known technique and is therefore not described in detail. A good treatment of decimation can be found in *Digital Filters and Signal Processing*, by Leland B. Jackson at pages 237–243. What is described is the rate of decimation because these choices are optimized to the display rates of the displays within the system and the resolution required of the analog output signals.

In the left branch of FIG. 5, the DSP executes a first rate change routine in step 186 that decimates the filtered patient monitoring data by a factor of two thereby reducing the effective sampling rate by one-half. Next, in step 188, the DSP executes a second rate change routine that further reduces the effective sampling rate by a factor of three. This decimated data, which has an effective sampling rate of one-sixth of the sampling rate of the A-to-D converter, is then transmitted to the A-to-D converter 66 over a synchronous SERIAL port 200 (FIG. 4) in step 190. The effective sampling rate is chosen to produce a resolution in the analog output signals generated by the A-to-D converter of 256 samples per second, which is the generally accepted resolution for these patient monitoring signals.

Concurrently with steps 186–190, the DSP decimates the filtered patient's monitoring signal data for display on the chart recorder and the liquid crystal display (LCD). The DSP first decimates the filter data by a factor of 11 in step 192. The effective sampling rate produced thereby is the resolution required by the chart recorder. Accordingly, in step 194, the output of step 192 is transmitted to the system processor over the AT_BUS which then forwards the data onto the chart recorder.

The output of step 192 is further decimated by a factor of two in step 196. This second decimation routine produces LCD display data that has an effective sampling rate optimized for the LCD display. The two decimation routines 192 and 196 produce an effective sampling rate such that each datum of the LCD display data corresponds to an individual pixel on the LCD display at a display rate of 25 millimeters per second, which is the accepted display rate for medical equipment. Thus, by choosing the A-to-D conversion rate and the decimation factors appropriately, the system minimizes the number of routines necessary to produce the required display data.

Medical monitoring equipment utilizing patient electrodes always picks up large amounts of line frequency interference through the patient electrodes. When the line frequency is known, standard adaptive finite impulse response (FIR) notch filter effectively removes this interference. Alternatively, if a sample of the line frequencies available, e.g., from a transformer tap, then this may be used with the adaptive notch filter to remove the interference.

In international product applications, the line frequency depends upon the country. If no sample of the line frequency is available, such as in low cost equipment, it would be most desirable to use an adaptive filter which determines the line frequency and then cancels the interference. Preferably, this filter should be a FIR filter in order to not disturb the desired signals' phase properties. The traditional LMS algorithm may be used to develop a filter capable of identifying the line frequency interference and rejecting it. The following description describes such an implementation according to the invention.

Following the procedural outline in Woodrow and Sterms, *Adaptive Signal Processing*, at pages 99, 100 and 101, the line frequency component may be estimated as follows:

$$\text{phase}+=\text{the } \Delta \quad (1)$$

$$EST = A \times \cos(\text{phase}) + B \times \sin(\text{phase}) \quad (2)$$

where A, B and $\Delta$ are parameters to be adjusted at each iteration

Given initial values of A, B, phase and $\Delta$, the above estimate of the data is then used with the new data value to compute an error value as follows:

$$\text{diff} = (\text{data} - EST) \quad (3)$$

$$err = \text{diff}_2 \quad (4)$$

We want to minimize the err function with respect to A, B, and phase. The gradient of err produces a vector in the direction of maximum increase, i.e.:

$$grad(err) = 2 \times diff \times \{\cos(\text{phase}) \times a + \sin(\text{phase}) \times b + \quad (5)$$
$$[B \times \cos(\text{phase}) - A \times \sin(\text{phase})] \times \delta\}$$

Where a, b and $\delta$ are unit vectors for the respective variables. We then apply a small amount of the negative of this gradient vector to the Current coordinate values (A, B and $\Delta$). Thus, the three variables are related as follows:

$$a \cdot A + b \cdot B + \delta \Delta -= \beta \times grad \text{ (err)} \quad (6)$$

or $$A -= \beta \times diff \times \cos \text{ (phase)} \quad (7)$$

$$B -= \beta \times diff \times \sin \text{ (phase)} \quad (8)$$

$$\Delta -= \times diff \times [i \, B \times \cos \text{ (phase)} - A \times \sin \text{ (phase)}] \quad (9)$$

where $\beta$ is a constant that determines the rate of convergence.

The variable $\Delta$ is proportional to frequency. Thus, by adjusting this variable the frequency of the estimated signal EST can be adjusted to track or adapt to the frequency of the data. The equation relating the frequency F of the estimated signal EST (i.e., the filter) can be derived as follows:

$$F = \Delta \cdot F_s / CPC,$$

where $F_s$ is equal to the sampling frequency of the filter (in this case the A-to-D converter) and CPC is equal to the number of counts per cycle. In the preferred embodiment, equal to 1536 Hz and CPC is equal to 65536. This latter value was chosen so that a range of CPCs of 0 to 65536 would correspond to an angle of 0 to $2\pi$ radians.

Similarly, adjusting the variables A and B is equivalent to adjusting the amplitude and phase offset of an arbitrary sinusoid due to the following equivalence:

$$A\cos \text{ (phase)} + B\sin \text{ (phase)} = \alpha \cos \text{ (phase-offset)}$$

where $\alpha = (A^2 + B^2)^{1/2}$ and offset $= \arctan(B/A)$.

Figure 6:
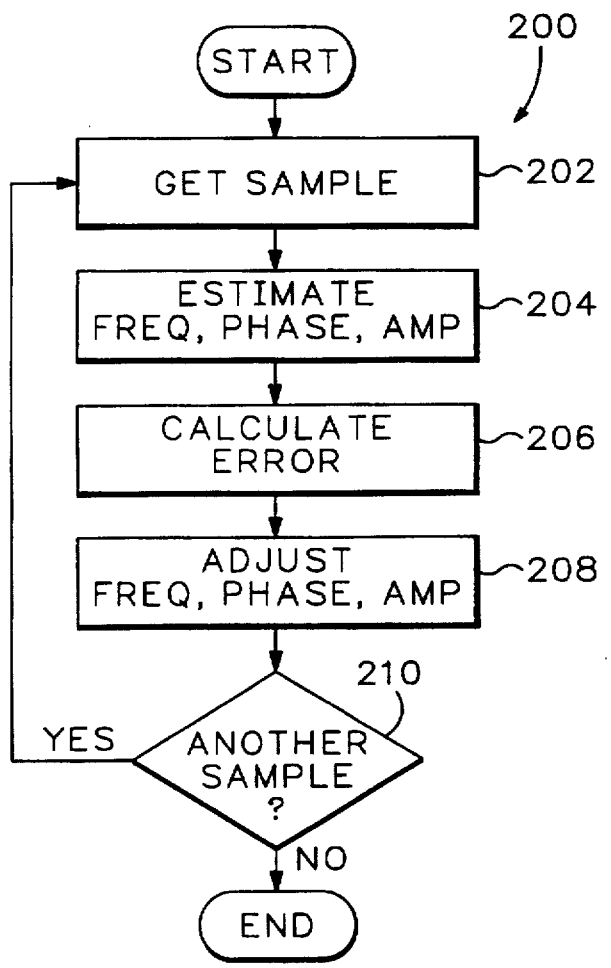
FIG. 6 is a flow chart of an adaptive filter according to the invention which is implemented by the digital signal processor shown in FIG. 4.

Referring now to FIG. 6, a flow chart of the frequency variable adaptive notch filter is shown generally at 200. The method shown is executed for each sample of the patient monitoring signals. It should be apparent that each patient monitoring signal is filtered independently of the others. The method shown, however, refers only to a single patient monitoring signal.

In step 202, a new data sample is read from the A-to-D converter by the digital signal processor. Next, the frequency, phase and amplitude of the signal is estimated in 204. These three parameters are estimated based on the formulas given above. An error (err) is calculated in 206 according to the formula (4) above. Finally, the frequency phase and amplitude are adjusted in 208 by recalculating the parameters (A,B,$\Delta$) according to the formulas (7–9) shown above. This sequence is repeated for each data sample. A C++ implementation of a filter based on these principles is shown in Appendix A.

F. LCD DISPLAY SECTION (FIG. 7)

Figure 7:
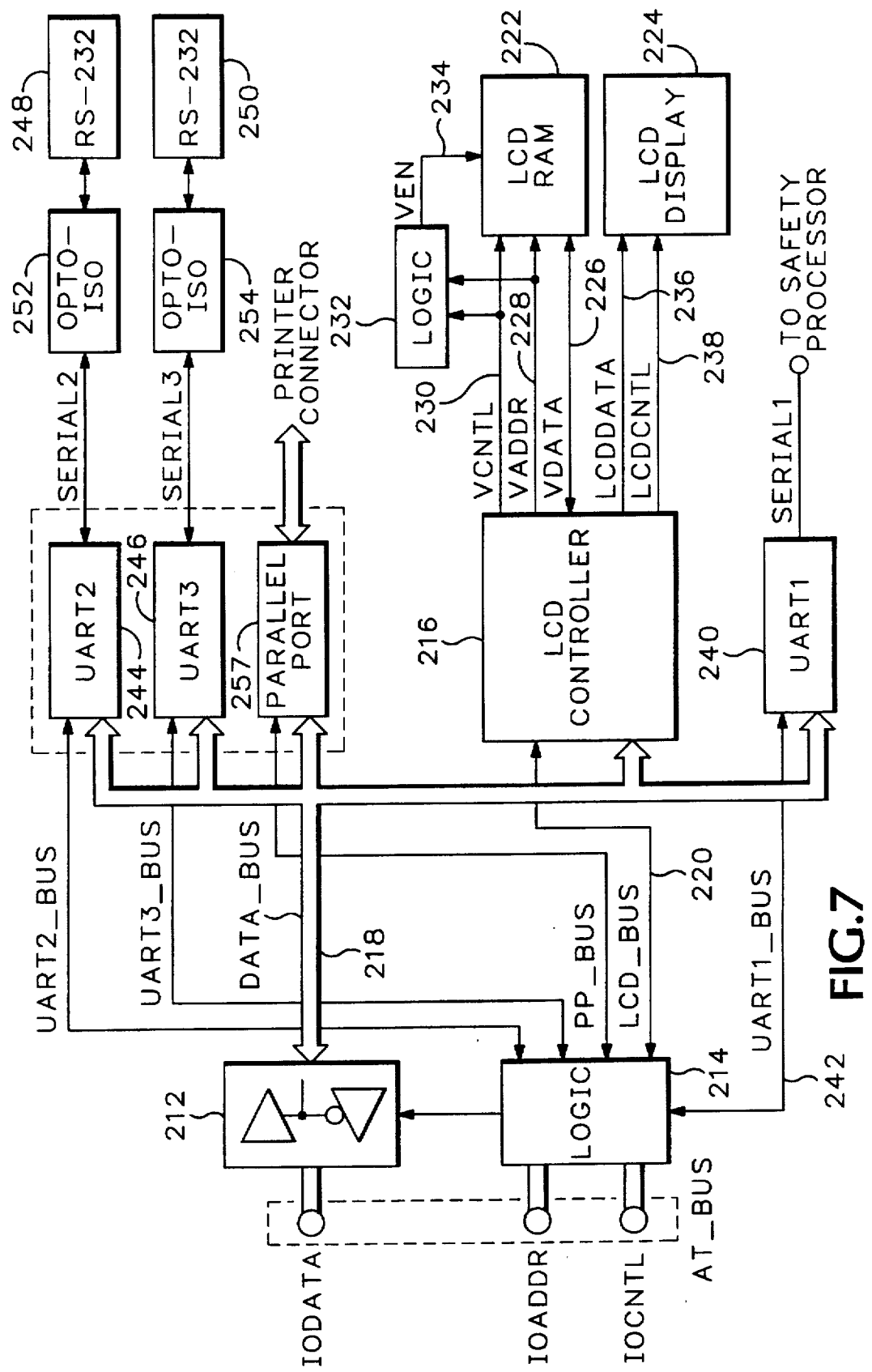
FIG. 7 is a block diagram of the liquid crystal display (LCD) and output ports of the system shown in FIG. 1.

Referring now to FIG. 7, a more detailed schematic diagram of the LCD display section is shown. In addition, the two serial ports (SERIAL2, SERIAL3) and a parallel port (PRINTER CONNECTOR) are shown. All of these components interface to the system processor over the AT_BUS, which is provided over the back plane. A set of bidirectional buffers 212 are interposed between the AT data bus IODATA and the other components in FIG. 7. A logic block 214 is coupled to the AT address bus IOADDR and the AT control bus IOCNTL. The logic box 214 decodes the address on the address bus IOADDR responsive to the control signals on the 10 bus IOCNTL according to a predetermined memory map in which the components in FIG. 7 are mapped.

The LCD display section includes an LCD controller 216, which is an industry standard part. The LCD controller communicates with the system processor over DATA BUS 218. The system processor communicates with the LCD controller using the AT bus protocol, as is well known in the art.

The system processor writes data and commands to the LCD controller over the AT_BUS, which commands are decoded by the logic block 214 and whose data is allowed to pass through the bidirectional buffers 212 and into the LCD controller 216 via DATA BUS 218. The logic block 214 enables the LCD controller 216 to receive this data by asserting the appropriate control signals on LCD bus 220. The LCD controller 216 is essentially in a master/slave relationship with the system processor wherein the LCD controller is the slave.

The LCD controller 216 is coupled to an LCD RAM 222 and to an LCD display 224. The LCD RAM 222 stores the display data which is communicated to the LCD controller by the system processor. The LCD controller 216 reads and writes data to the LCD RAM 222 over a DATA BUS 226. The LCD controller specifies the address of a particular LCD RAM location by providing an address on address bus 228 and asserting appropriate control signals on control bus 230 and logic block 232 enables the LCD RAM 222 by asserting enable signals on bus 234 responsive to the appropriate address and control signals on buses 228 and 230.

The LCD controller 216 provides the display data stored in LCD RAM 222 to the LCD display 224 over DATA BUS 236 by asserting the appropriate signals on control bus 238.

As described above, the LCD display has a particular resolution defined as so many pixels per inch. The LCD display further includes a predetermined display rate which defines the rate at which data, and particularly signal data, moves across the LCD screen. The decimation routines described above are designed so that each datum produced by the decimation routine can be displayed on a single LCD pixel at a display rate of 25 millimeters per second, which corresponds to the well-accepted industry standard display rate. This avoids having to do any interpolation to produce the desired display rate.

Also shown in FIG. 7, is a UART 240 which is interposed between the system processor 38 and the safety processor 40 (FIG. 1A). The UART 240 provides a serial interface (SERIAL1) between the system and safety processors to allow communication there between. The UART 240 is another memory mapped peripheral on the AT_BUS, as is the LCD controllers and others. The UART 240 therefore communicates with the system processor over DATA BUS 218 and is selected or enabled by appropriate signals being asserted by logic block 214 on UART bus (UART1_BUS) 242.

The other two serial polls (SERIAL2, SERIAL3) are also shown in FIG. 7. Two additional UARTs 244, 246 provide these two serial interfaces. The UARTs 244,246 communicate with the system processor in a conventional manner over the AT_BUS as does UART 240. The UARTs 244 and 246 are isolated optically from external RS-232 interfaces 248 and 250 by opto-isolators 252 and 254, respectively. The UART 244 is used to provide digital patient information to an external peripheral over a standard RS-232 connection. The other UART 246 is used to provide miscellaneous other data that can be monitored and/or stored on a computer or peripheral.

Also shown in FIG. 7 is a parallel port 257 through which the system processor provides data to an external printer. The parallel port 257 provides a standard Centronix type connection.

UARTs 244 and 246 and parallel port 257 are enclosed by a broken line to indicate that, although these are separate functions, they can be contained within a single component such as a 16C552.

G. FRONT PANEL SECTION (FIG. 8)

Figure 8:
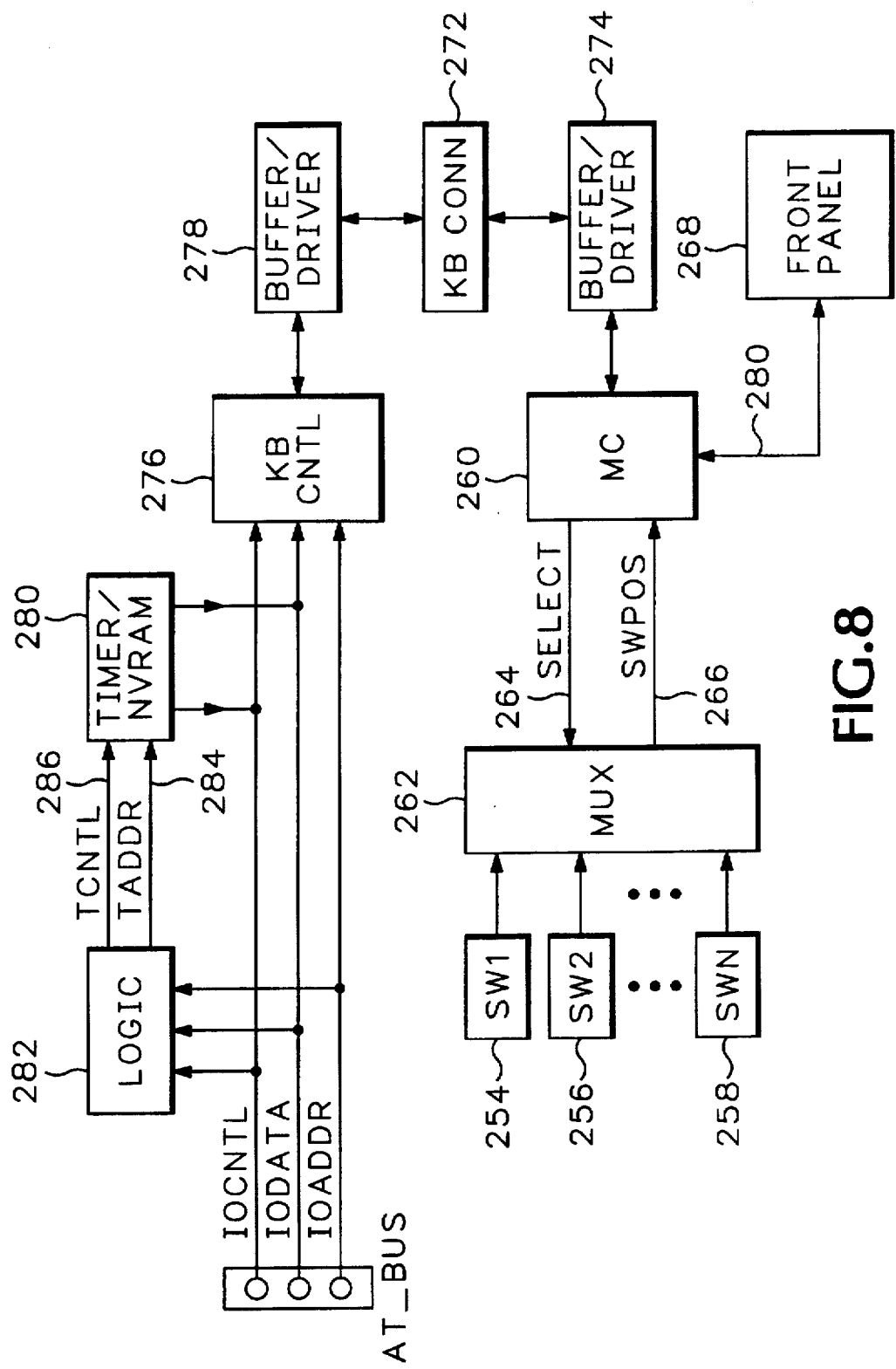
FIG. 8 is a block diagram of the front panel and NVRAM section of the system shown in FIG. 1.

Referring now to FIG. 8, a block diagram of the front panel section is shown. The front panel includes a plurality of switches 254, 256 and 258, which are used to specify or reset the parameters of the ECT pulse treatment. These parameters include frequency, pulse width, current and treatment duration, among others. Any number of relevant settings can be provided in this manner. The front panel section includes a microcontroller 260, which in the preferred embodiment is an 8051 microcontroller. Because of the limited number of inputs provided on microcontroller 260, a multiplexer 262 is interposed between the switches 254–258 and the microcontroller 260. The multiplexer provides one of the switch settings to the microcontroller depending upon a SELECT signal on a select bus 264. The switch position for the selected switch is communicated to the microcontroller over the switch position bus 266. In this way, only a single set of inputs on MC 260 is required to read all of the switch positions. If sufficient inputs were available on MC 260, however, the MUX 262 could be eliminated.

The microcontroller 260 is also coupled to the front panel itself 268 through which commands are input to the system. The microcontroller 260 communicates with the front panel 268 over bus 280.

An industry standard keyboard connector 272 is provided through which the microcontroller 260 communicates with the system processor. A buffer/driver circuit 274 is interposed between the microcontroller 260 and the keyboard connector 272 to provide the necessary signal conditioning required by the industry standard keyboard interface. The microcontroller communicates with the system processor as if the microcontroller 260 were a keyboard. This interface was chosen so that during development, the front panel section could be replaced by an actual keyboard to allow for efficient input of commands to the system controller by simply pressing the desired key.

On the other side of the keyboard connector 274 is an industry standard keyboard controller 276 which receives the keyboard commands from the microcontroller 260 and communicates these commands to the system processor over the AT_BUS. The keyboard controller 276 in the preferred embodiment is an 8042 industry standard controller. The keyboard controller 276 also includes a buffer driver circuit 278 that places the keyboard commands in the appropriate format in order to be received by the keyboard controller 276. The keyboard controller 276 then communicates the received keyboard commands from the microcontroller 260 using the conventional keyboard protocol. In this way, the system processor need only use a standard keyboard processing routine to receive commands from the front panel interface section.

Also shown in FIG. 8 is a timer and non-volatile RAM (NVRAM) circuit 280, which is also coupled to the AT_BUS. The timer and NVRAM circuit 280 are mapped into the system processor's memory space, as is the keyboard controller 276. A logic block 282 decodes the address and control signals provided on the AT_BUS and enables the timer and NVRAM circuit accordingly. In this way, the system processor can communicate to and front the timer and NVRAM circuit over the AT_BUS. The logic block 282 includes a set of latches which latch an address provided on the AT data bus IODATA and provide this address (TADDR) to the timer NVRAM circuit over a dedicated address bus 284. The timer and NVRAM circuit 280 then provides the data corresponding to this address on the AT data bus IODATA responsive to control signals received on the timer and NVRAM control bus 286. In the preferred embodiment, the timer and NVRAM circuit includes a DS1386 part manufactured by Dallas Semiconductor.

H. DIGITAL-TO-ANALOG CONVERTER SECTION (FIGS. 9–10)

Figure 9:
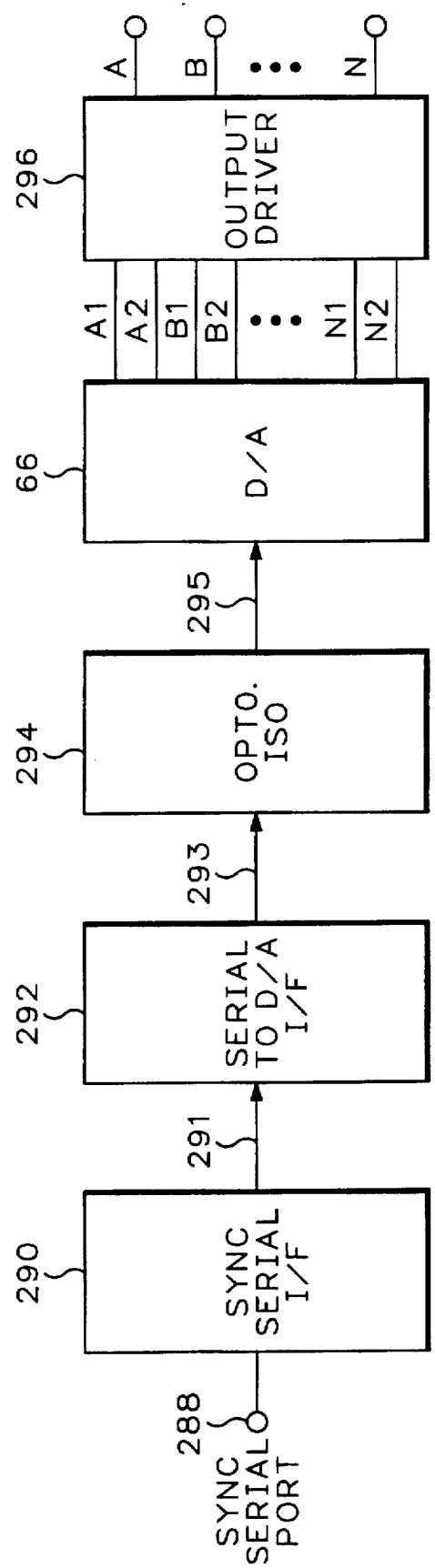
FIG. 9 is a block diagram of the digital-to-analog converter section of the system shown in FIG. 1.

Referring now to FIG. 9, a detailed block diagram of the digital-to-analog (D-to-A) converter section is shown. As described above, the digital signal processor 42 provides its filtered and decimated data to the isolated data output section 60 so that the patient monitoring signals can be displayed or captured by an external device. This data is provided over a synchronous serial port 288. Coupled to the serial port 288 is a synchronous serial interface circuit 290 that receives the serial data from the digital signal processor. An output bus 291 is coupled between the synchronous serial interface and a serial to D-to-A interface circuit 292. The bus 291 includes the standard transmit and receive signals that comprise a serial interface. The circuit 292 converts the serial inputs to a format required by the D-to-A converter 66. The D-to-A converter 66 is optically isolated from the circuit 292 by an opto-isolator circuit 294, which is known in the art.

The D-to-A converter 66 includes a plurality of output channels, which are coupled to an output driver 296. The design of the D-to-A converter and output driver shown in FIG. 10 is well-known in the art and is therefore not discussed further.

Figure 10:
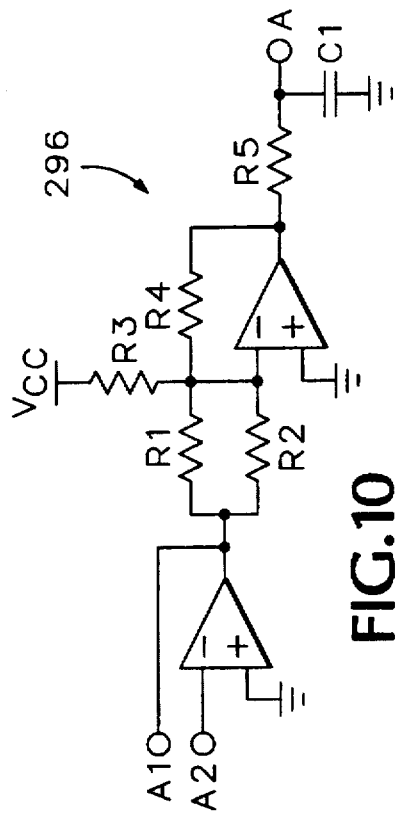
FIG. 10 is a schematic diagram of the output driver shown in FIG. 9.

The circuit shown in FIG. 10, however, is repeated for each of the outputs of the D-to-A converter. In the preferred embodiment, there are eight analog outputs, i.e., N = 8.

1. SAFETY MONITORING SECTIONS (FIGS. 11–13)

The heart of the safety features of the system is shown in FIGS. 11–13. Before discussing the safety features, however, we will first discuss the ECT pulse generator circuit.

Figure 12A:
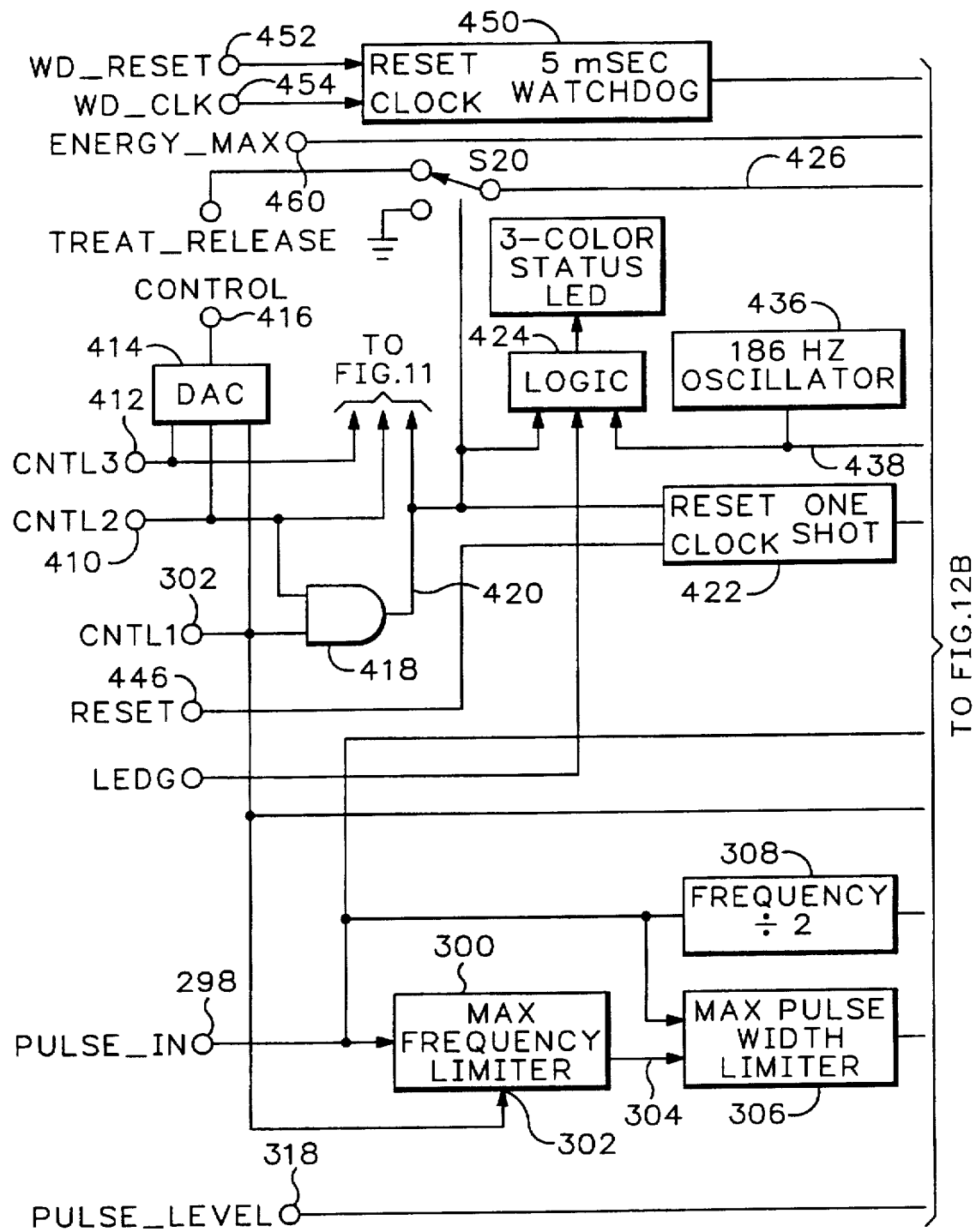
FIGS. 12A and 12B are block diagrams of further portions of the safety monitoring sections of the system shown in FIG. 1.

Referring now to FIG. 12A, the safety monitoring circuit shown therein includes an input 298 for receiving an input signal PULSE_IN. This signal is generated by the safety processor each time a treatment pulse is to be generated. The pulse width of this signal is set from the front panel by adjusting the appropriate knob to the desired setting. This setting is then read by the safety processor, which generates the pulse width accordingly. In the preferred embodiment, two timers are used to form the pulse width and frequency of the signal PULSE_IN.

The user can also set the frequency of the treatment pulse train by setting the appropriate knob on the apparatus. This frequency setting determines the period between the leading edge of the successive treatment pulses. In addition, the user can set the total duration of the treatment pulse train, which is the duration of the ECT treatment. The user can also set the current level in a similar manner.

The PULSE_IN signal is provided to a maximum frequency limiter circuit 300, which limits the frequency passed on to the ECT driver circuits to a maximum frequency as specified by the circuit 300. If the frequency of PULSE_IN exceeds this frequency, the limiter inhibits generation of further ECT pulses. In the preferred embodiment, this frequency limiter circuit 300 is implemented by a retriggerable one shot, e.g., 14538, whose RC time constant sets the maximum frequency of the circuit. The input 298, in that case, is connected to the positive edge trigger input (+T) of the one shot. The reset input (R) of the one shot is connected to a control input 302 for receiving a control signal CNTL1 from the safety processor. Thus, the safety processor can prevent the frequency limiter circuit from passing on any pulses by asserting this signal. The frequency limiter circuit 300 produces an output on line 304 whose leading edges track the leading edges of input PULSE_IN if the frequency of the input signal is less than the maximum frequency limit of the circuit and has a frequency equal to zero if the input pulse frequency exceeds that maximum frequency.

The output of the max frequency limiter 300 is connected to a max pulse width limiter circuit 306. The limiter circuit 306, as limiter 300 did for frequency, limits the pulse width of the pulses passed on to the ECT driver circuits to a predetermined maximum pulse width. If the pulse width of PULSE_IN exceeds the maximum pulse width, limiter 306 limits the pulse width to the maximum predetermined pulse width. This limiter 306 in the preferred embodiment is also implemented using a one shot, e.g., 14538, but in a nonretriggerable mode. The maximum pulse width is set by the RC time constant of the one shot. The inverted output of the one shot is connected to the negative edge trigger input of the one shot (–T) to prevent retriggering, and the reset input (R) is connected to input 298 to receive the input PULSE_IN. When the width of PULSE_IN is less than the timeout period of one shot 306, the normal case, the latter connection causes the width of pulse passed on to the ECT driver circuits to be equal to the pulse width of $PULSE_{13}$ IN.

The input PULSE_IN is also provided to a frequency divider 308, which divides down the input pulse rate by a factor of two. The output of the frequency divider 308 is coupled to a first select input of the analog MUX 310 on line 312. Similarly, the output of the pulse width limiter 306 is coupled to a second select input of the analog MUX 310 via line 314. Line 314 is also connected to a pulse extender 316 which delays the trailing edge of the pulse to provide a longer pulse signal STRETCHED PULSE that is used to disconnect the patient monitoring signals from the input section when each treatment pulse is applied. The pulse extender is described further below.

The analog multiplexer 310 also includes two analog inputs. The first one of these inputs is connected to input 318 for receiving a signal PULSE_LEVEL, which establishes the output current level of the ECT pulse. Another one of the analog multiplexer inputs is connected to a fixed voltage source of –0.5 volts. The signal levels on the select inputs of the MUX determine which of the two inputs is passed through to the multiplexer outputs OUT1 and OUT2. Configured in this way, the outputs are responsive to the input pulse PULSE_IN.

The first output of the analog MUX OUT1 is connected to the non-inverting input of amplifier 320. Similarly, the second output OUT2 is connected to the non-inverting input of amplifier 322. The inverting inputs of both amplifiers 320 and 322 are connected to the emitters of output transistors Q1 and Q2. The outputs of amplifiers 320 and 322 are connected to drive output transistors Q1 and Q2, respectively by means of power MOSFET transistor drivers (not shown) one connected to the base of Q1 and another to the base of Q2 in the darlington configuration. Power is provided to both amplifiers 320 and 322 from a 20 volt regulator 324 through a switch S10. The switch S10 provides either the 20 volt supply voltage to the amplifiers on line 328 or a ground signal depending upon the state of switch S10, which is controlled by logic gate 326. Thus, logic gate 326 can remove power from the output amplifiers depending upon the state of its inputs. This is a safety feature, which is described further below.

A current limiting circuit 330 clamps the output voltage of the amplifiers 320 and 322 if the currents through output transistors Q1 and Q2 exceed a predetermined current limit. The collectors of Q1 and Q2 form the two outputs for generating the ECT pulses. A third output is provided by a 33 volt regulator 332. These three outputs connect to the center-tapped primary winding of transformer T1 shown in FIG. 11A.

Figure 11A:
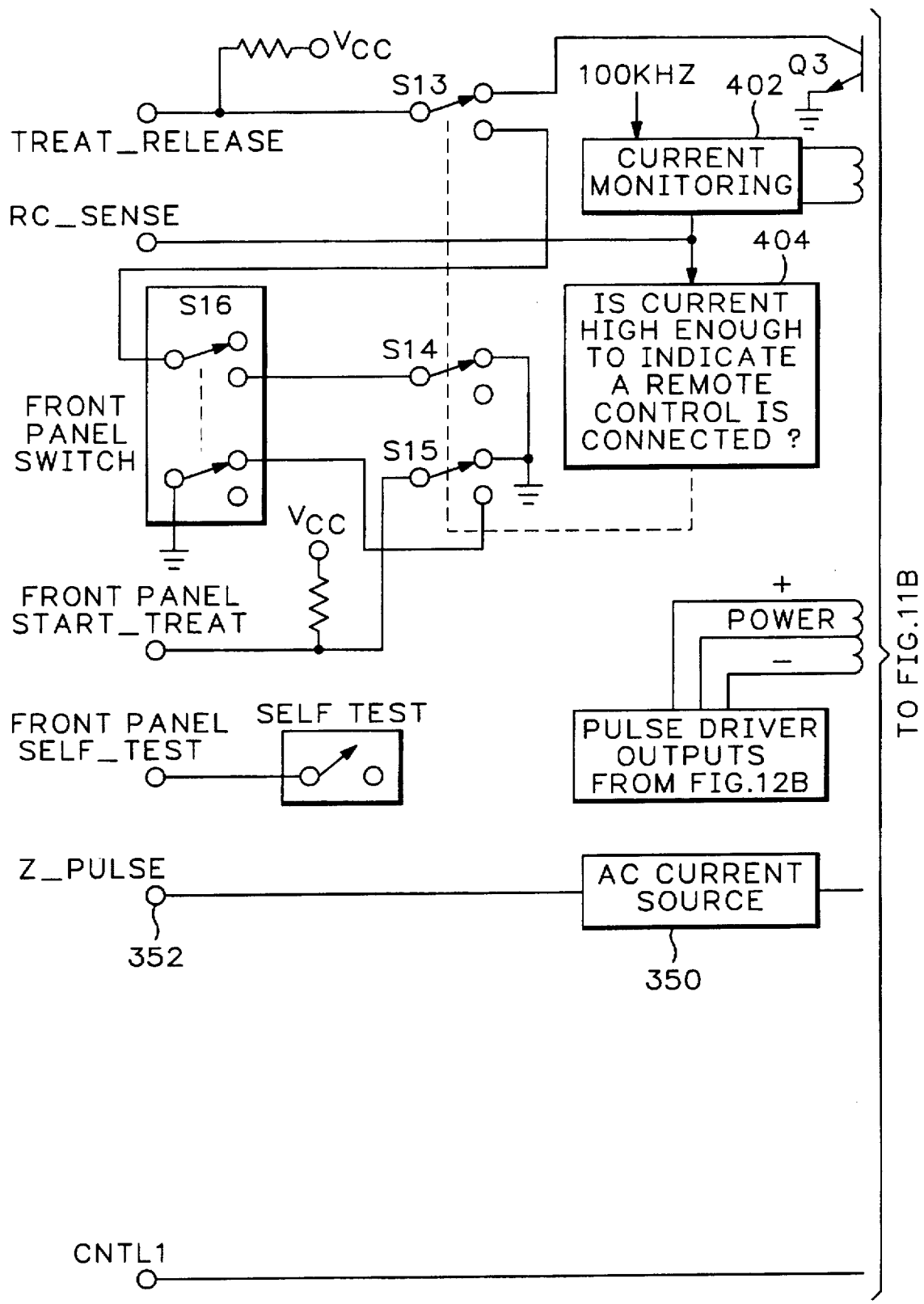
FIGS. 11A and 11B are block diagrams of the delivery means and hardware safety monitors of the system shown in FIG. 1.

Referring to FIG. 11A, the three outputs (+,–, and POWER) are connected to the center-tapped primary winding of transformer T1. Transformer T1 is a step up transformer so that the voltage across the secondary winding (FIG. 11B) is equal to the turns ratio times the voltage across the primary. The current in the secondary, on the other hand, is reduced by the turns ratio. In the preferred embodiment, the turns ratio is equal to 16.6:1.

A relay R1 is interposed between the outputs of the secondary winding and two paddles 334 and 336. The paddles are shown with the optional remote control unit 338. Alternatively, paddles 334 and 336 could be simple electrodes that are used when the treatment is initiated from the front panel as described further below.

The relay R1 is used to switch a dummy load R7 into and out of the circuit of the secondary winding of T1. When the relay is in the position shown in FIG. 11 B, the dummy load is switched into the circuit and when the relay is in its other position, the dummy load is taken out of the circuit and the winding is connected to the. paddles 334 and 336. The state of the relay is controlled by a logic gate 338 whose output is connected to the coil of the relay via line 340. The logic gate 338 includes two inputs 342 and 344 for receiving a hardware shutdown signal HW_SD (FIG. 12B) and a control signal CNTL2 (FIG. 12A). The logic gate 338 switches from the dummy load to the patient, i.e., the paddles, if the control signal CNTL2 is asserted and the hardware shutdown signal HW_SD is not asserted. This provides the system with the ability to shunt the pulse to a dummy load under software control as indicated by the assertion of the control signal CNTL2, which is under control of the safety processor. The control signal CNTL2 allows the system to perform an internal self-test in which a pre-treatment pulse train is applied to the dummy load and the characteristics of the pulses are then examined by the safety hardware and the system rendered inoperable if any of these safety tests fail.

The safety monitoring section also includes a second relay R2 (FIG. 11B), which is used to either short out, or leave unshunted, a 10 K ohm resistor R8 in the output circuit under certain test conditions. This 10 K ohm load is shorted by R2, thus effectively shorting the secondary winding of transformer T1 when a control signal CNTL3 is asserted. This control signal is applied to the coil of relay R2 via input 346. The 10 K resistor and relay R2 are used during the self-tests of the instrument's ability to measure static impedances at zero ohms and 110 K ohms.

A second transformer T2 is used to measure the voltage delivered to the dummy load during pre-treatment testing. The voltage across the primary of T2 is stepped down to the secondary, which is then measured by a voltage monitoring circuit 348. A current is provided to the secondary winding by an AC current source 350, which generates a fixed current responsive to the Z_PULSE received on input 352. This causes a current of approximately 40 µA through the secondary of T2. Because the current AC amplitude is fixed, then the voltage measured by the voltage monitoring circuit 348 is proportional to the static impedance (of the patient or of the impedance self-test resistor R8). The measured voltage DELIV_V is provided to the safety processor from the voltage monitoring circuit on output 354. A signal corresponding to the measured impedance IMP is provided by the voltage monitoring circuit to an amplifier 356 whose output is then rectified by precision rectifier 358 and filtered by low pass filter 360. The output of low pass filter 360 is a signal Z on output 362 that is proportional to the measured static impedance.

The circuits described above measure what is termed "static" impedance. Static impedance in the context of ECT is the impedance measured under test conditions of very low currents applied to the patient (or test resistors). Static impedance changes little with continued application of the current used to perform the measurement. "Dynamic" impedance in the context of ECT, on the other hand, is the effective impedance presented by the patient's scalp and the paddle electrodes to the applied treatment current. Dynamic impedance is the impedance observed at very high applied currents, where the scalp tissue exhibits non-linear impedance behavior. The dynamic impedance seen in ECT is much lower than the static impedance seen in ECT, and furthermore, decreases generally during the duration of the treatment. Dynamic impedance is calculated by the system processor by dividing the delivered voltage by the delivered current. Signal Z on line 362 is not used to obtain dynamic impedance.

The circuit also includes another transformer T3, which is used to measure the current through the output circuit of T1. The transformer T3 is a (voltage) step up transformer whose secondary is coupled to a current monitoring circuit 364 which measures the current through the output circuit. This measured current signal DELIV_I is then provided to the safety processor on output 366.

The circuit also provides an energy monitor circuit. The energy monitor includes an analog multiplier 388, a voltage-to-frequency converter 390, a two-stage counter 392 and an energy limit select circuit 394. The analog multiplier has two inputs: one of which is connected to the voltage monitoring circuit 348 to receive the measured voltage signal DELIV_V; and the second input is connected to the current monitoring circuit 364 to receive the measured current signal DELIV_I. The analog multiplier then multiplies these two signals together to produce a delivered power signal DELIV_P on output 396. The delivered power signal is then provided to a voltage-to-frequency converter 390 which converts the voltage level of the delivered power signal to a clock signal having a frequency proportional to that power signal level. The clock signal is provided to a clock input of a counter 392, which in the preferred embodiment is implemented by cascading two binary counters. The counters produce a binary count that increments with each rising edge of the clock signal from the voltage-to-frequency converter 390. This binary count is then provided to a maximum energy limit select circuit 394 which compares the binary count to a preset limit. If the binary count exceeds this preset limit, the circuit 394 asserts a signal ENERGY_MAX on output 398 to indicate that the amount of energy delivered to the patient during this treatment has exceeded the preselected limit. In the preferred embodiment, the limit is adjustable with the use of jumpers to allow for different limits to be set in different countries or under different conditions. It should be apparent that the voltage-to-frequency converter and counter are but one implementation of what is essentially an integrator, which integrates the delivered power signal DELIV_P over time. Other integrators, of course, can be used.

Figure 11B:
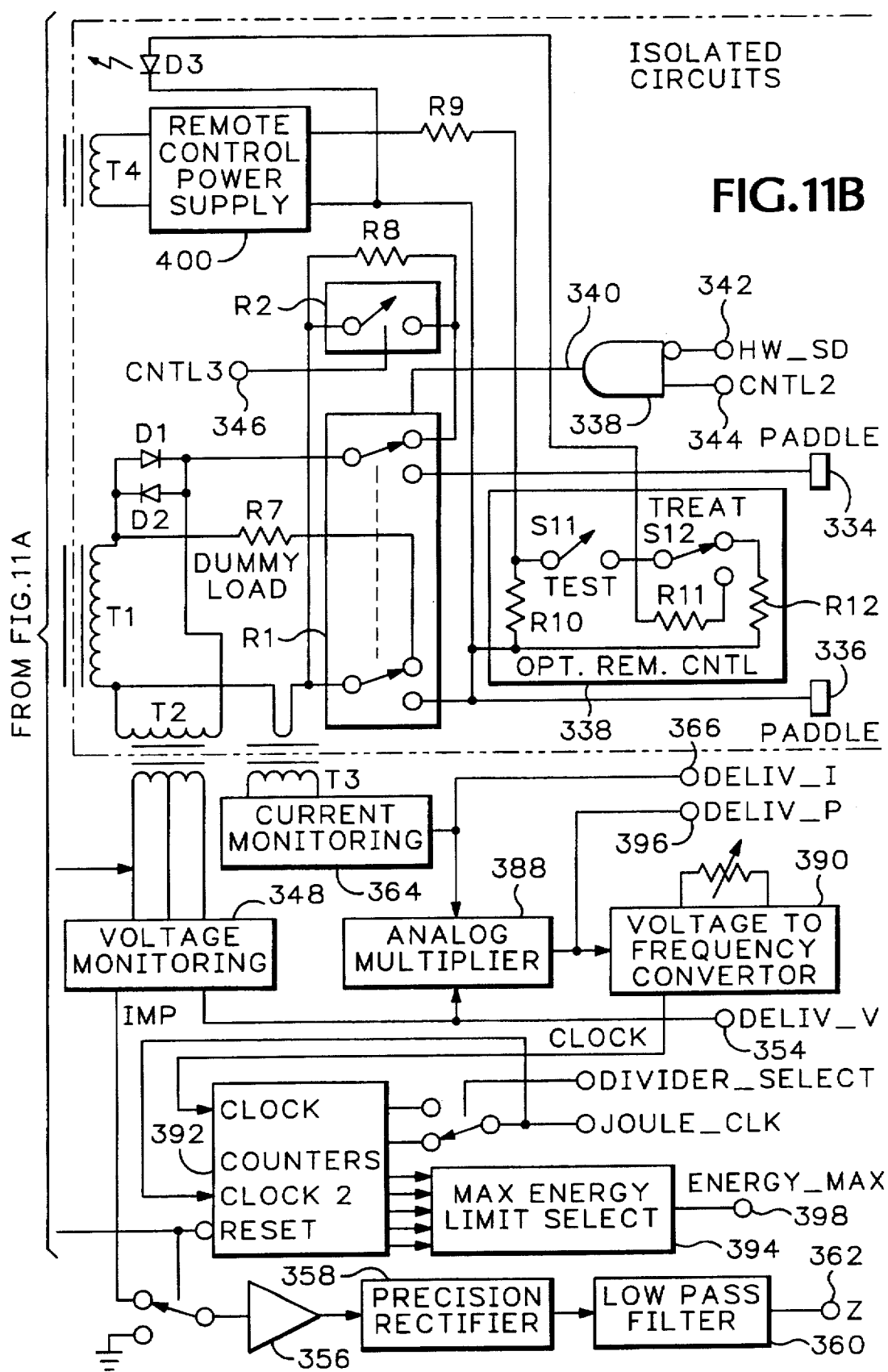

The paddles 334 and 336 are part of an optional remote control package that allows the user to initiate an ECT treatment from the paddles. Otherwise, the user can only initiate a treatment from the front panel start treatment switch. One of the paddles includes a two-stage switch represented by switches S11 and S12 in FIG. 11B. The first switch S11 initiates a pre-treatment test sequence. Actuation of switch 11 is detected by measuring the current through the optional remote control unit. This is accomplished by switching different resistances into the circuit according to which switch is actuated. Switch S11 is normally open, as indicated in FIG.11B. In addition, switch S12 is normally in the position shown. In this default state, a circuit is formed with resistors R9 and R10 across which a voltage is supplied by remote control power supply 400. The current supplied by the power supply 400 is detected by a current monitoring circuit 402 which is coupled to the power supply 400 by a transformer T4. The current monitor 402 produces a signal RC_SENSE, which is proportional to the measured current supplied by the power supply 400. This signal RC_SENSE is provided to a threshold detector 404, which compares the current level of the signal $RC_{13}$ SENSE to determine whether the current level exceeds a predetermined amount. If insufficient current is detected, the circuit 404 assumes that the remote control unit is not connected. If the circuit, however, detects this minimum current level, then the circuit 404 switches the state of switches S13, S14 and S15 so as to disable the front panel switch S16, which is also used to initiate a treatment sequence.

If the test switch S11 is actuated, on the other hand, resistor R12 is coupled in parallel with resistor R10, thereby presenting a different load to the remote control power supply 400. This current is also measured by the current monitor 402.

The treatment switch S12 actually corresponds to the second stage of the two-stage switch comprised of S11 and S12. Therefore, S12 can only be actuated if S11 is also actuated. If S12 is actuated (and therefore S11), a circuit is formed with R9, R11 and light-emitting diode D3 of an opto-coupler. Passing a current through diode D3 causes a signal to be produced by optical detector Q3, which is then passed on to the safety processor as the TREAT_RELEASE signal through switch S13. This signal can then be used to determine if the treatment switch S12 is released prior to the full treatment duration that was programmed by the front panel controls.

Referring again to FIGS. 12A and 12B, three control signals CNTL1, CNTL2 and CNTL3 are shown being received at inputs 302, 410 and 412, respectively. These input signals are provided to a D-to-A converter 414 which produces an analog signal control on DAC output 416, which reflects the signal levels on the three control signals. The DAC 414, in the preferred embodiment, is a simple resistive summing circuit that adds the binarily weighted control signals CNTL1–CNTL3 to produce the analog control signal CONTROL on output 416. This control signal is then read by the safety processor to verify the state of the control signal CNTL1–CNTL3. This provides an additional check to ensure that the system is configured in the manner desired by the safety processor.

Control signals CNTL1 and CNTL2 are provided to an AND gate 418 that logically ANDs these two signals together (CNTL1 and CNTL2 are high at the same time only during a patient treatment mode) to produce an output signal on line 420 that is coupled to a control input of switch S20, a reset input of one shot 422 and an input of logic block 424. Switch S20 provides either a ground signal on line 426 or a treatment button release signal TREAT_RELEASE, which is asserted when the selected start treatment switch is prematurely released. Line 426 is then coupled to an input of an OR gate 428, whose output 430 is a hardware shutdown signal HW_SD. This hardware shutdown signal immediately removes power from output amplifiers 320 and 322 by causing switch S10 to switch through gate 326. Thus, the pulse output amplifiers will be disabled whenever (1) either CNTL1 or CNTL2 is deactivated (treatment finished normally, and the safety processor has caused the disabling intentionally), or (2) when the selected treatment switch is released prematurely during a treatment, or (3) a fault condition such as maximum energy is reached.

The OR gate 428 also includes another input for receiving a timer expired signal TIMER_EXPIRED on line 432. This signal is generated by a ten-second timer 434, which asserts the signal any time the timer exceeds ten seconds without being reset. The timer 434 includes a clock input that is driven by a 186 Hz oscillator 436, which produces a clock signal on line 438. This clock signal is gated by logic gate 440, which allows the clock signal to pass through to the clock input of the timer as long as the hardware shutdown signal HW_SD is not asserted. If the hardware shutdown signal HW_SD is asserted, logic gate 440 blocks the clock signal. This prevents the timer 434 from being incremented following a hardware shutdown. This further allows the system to determine what was the cause of the hardware shutdown, e.g., expiration of timer 434. The reset input of the timer 434 is driven by a logic block 442 that has two inputs: a first input coupled to an Output of one shot 422; and a second input coupled to input 298 to receive the signal PULSE_IN. As described above, the PULSE_IN signal is asserted during each pulse. The one shot 422, on the other hand, produces an output signal on line 444 at the end of each ECT pulse train responsive to a reset signal RESET on input 446. The logic block 442 contains a latch (not shown) which holds a reset signal on line 448 until that latched reset is removed by the first pulse in an ECT pulse train. The timer 434 then runs from that point. The timer 434 continues to run until the conclusion of the treatment. If a fault occurs which allows the treatment duration to exceed ten seconds, the timer will expire thereby producing a hardware shutdown. Thus, timer 434 is a pulse train duration detector that prohibits or disables further treatment if the ECT pulse train duration exceeds the ten second maximum duration. As a safety feature, one shot 422 is prevented from resetting counter 434 during a patient treatment by gate 418, which holds one shot 422 in reset during the treatment.

The system also includes a watchdog timer 450 that has a reset input coupled to input 452 for receiving a watchdog reset signal WD_RESET and a clock input coupled to input 454 for receiving a watchdog clock signal WD_CLK from the safety processor. The watchdog timer 450 includes an output that is coupled to line 456 that is connected to output 458 and to one of the inputs of gate 428. The watchdog timer 450 produces a watchdog failure signal WD_FAILURE if the watchdog timer 450 is not clocked within a predetermined time following the last clock signal $WD_{13}$ CLK. The watchdog timer therefore causes a hardware shutdown if the watchdog timer 450 is not clocked within this time period.

The watchdog timer ensures that the safety processor is functioning properly. The safety processor includes a routine that is invoked periodically. Under control of that routine, the safety processor repeatedly clocks the watchdog timer. Thus, if the watchdog timer is not clocked, it means that the safety processor has failed to execute this routine as it was suppose to. The system therefore disables further treatment in that case. WD_RESET on 452 is activated at power up of the instrument, and for any other condition that would cause a reset of the system processor, e.g., logic supply voltage being too low.

Another condition that can produce a hardware shutdown is where the maximum energy (as set by regulatory organizations) for the ECT pulse train is exceeded. This condition is detected by energy limit select circuit 394, as described above. The output of circuit 394 is coupled to input 460 (FIG. 12A), which is then provided to one of the inputs of OR gate 428. The OR gate 428 in turn produces a hardware shutdown signal HW_SD if the output of the energy limit select circuit 394 is asserted (i.e., ENERGY_MAX).

The OR gate 428 includes an additional input that allows the hardware shutdown signal HW_SD to be fed back to its input switch S21 so that the system remains in the hardware shutdown state once that condition exists. The system can clear the hardware shutdown condition by clocking the one shot 422, which causes the switch S21 to switch between the hardware shutdown signal HW_SD and ground. The hardware shutdown condition will be cleared then assuming that none of the other hardware shutdown conditions (i.e., TIMER_EXPIRED, WD_FAILURE, ENERGY_MAX, TREAT_RELEASE) exist.

Figure 12B:
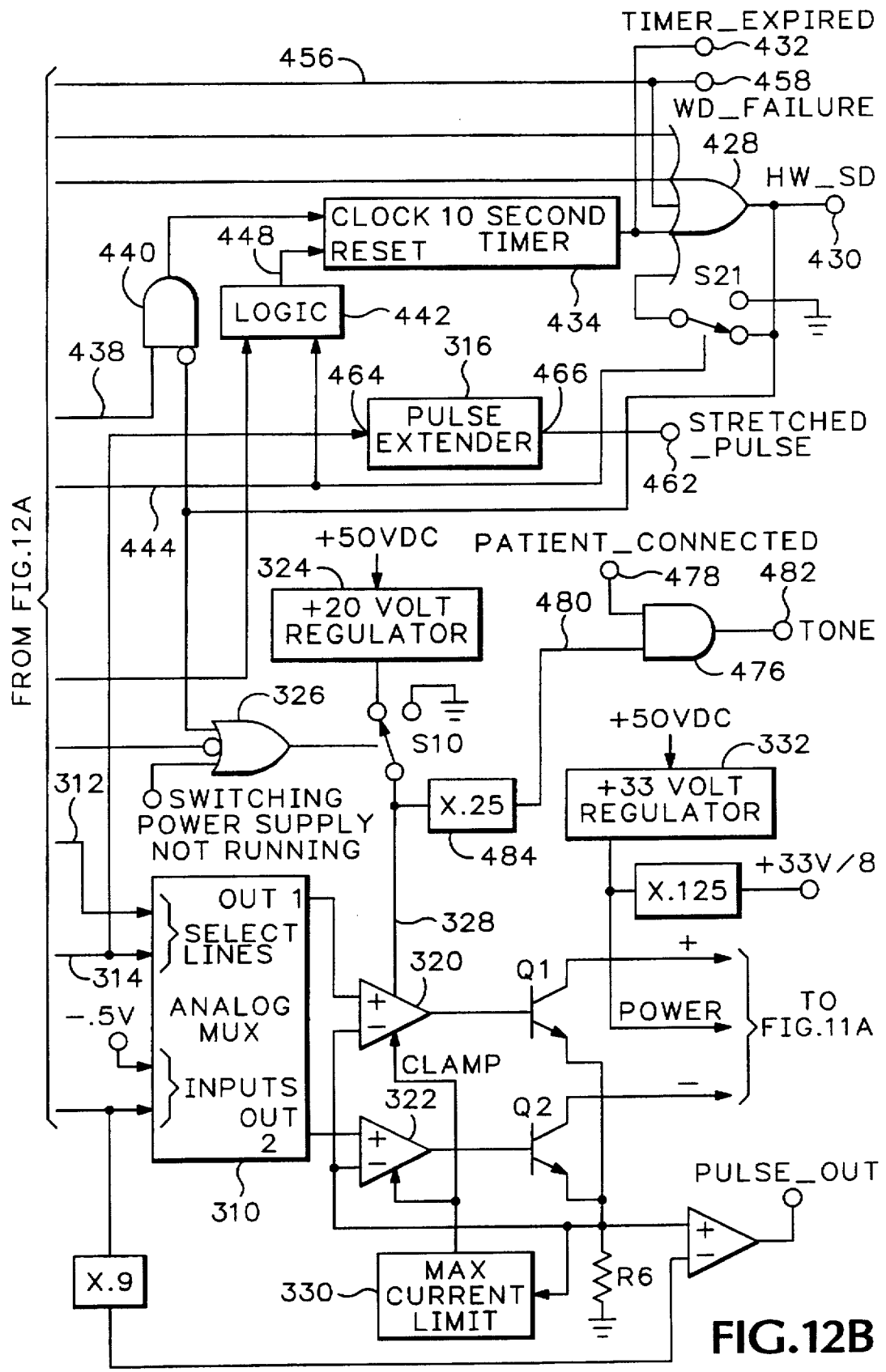

Referring again to FIG. 12B, a pulse extender circuit 316 is shown. This pulse extender takes the input pulse signal on line 314 and delays its trailing edge to produce the signal STRETCHED PULSE on output 462. This output, as described above, is used to inhibit reception of the patient monitoring signals during application of each ECT pulse. This allows for better response from the patient monitoring section (FIG. 3). A schematic of the preferred embodiment of this pulse extender circuit 316 is shown in FIG. 13. The circuit uses a 14538 one shot 468 and an RC network shown generally at 472. The one shot has two OR'd clock inputs;

the negative-edge-trigger clock input receives its input signal on line 314 from FIG. 12B. The other clock input of the one shot is connected to the non-inverting output (Q) of the one shot so as to prevent "retriggerability." The RC network is coupled to the RC input of the one shot. The time constant of these two components determines the amount of time by which the trailing edge of the output signal STRETCHED_PULSE is delayed relative to the trailing edge of the input signal on line 464.

Referring again to FIG. 12B, an AND gate 476 is included, which generates a tone signal TONE on output 482 when relay R1 (FIG. 11B) is connected to the paddles and power is supplied to the output driver amplifiers. The AND gate 476 includes two inputs: one of which is connected to input 478 to receive a patient connected signal PATIENT_CONNECTED, which is asserted when relay R1 is connected to paddles; and a second input coupled to a voltage divider circuit 484 that divides down the twenty-volt supply voltage produced by regulator 324 to provide a five-volt signal on line 480 when switch S10 is set to receive the supply voltage. The tone signal TONE then drives an audio indicator to inform the user of the current condition of the system. This purely-hardware path is a safety feature that operates independently of the system processor's means to drive the audio indicator.

II. OPERATION (FIG. 14)

A. TEST SEQUENCING (FIG. 14) The heart of the Applicant's invention is the advanced safety feature set included in the ECT apparatus. These safety features include both hardware and software safety detectors and monitors. Safety tests are performed during both pretreatment and treatment. This level of redundancy and frequency provides patient safety heretofore not found in ECT apparatus. The operation of these safety tests is now discussed.

Figure 14:
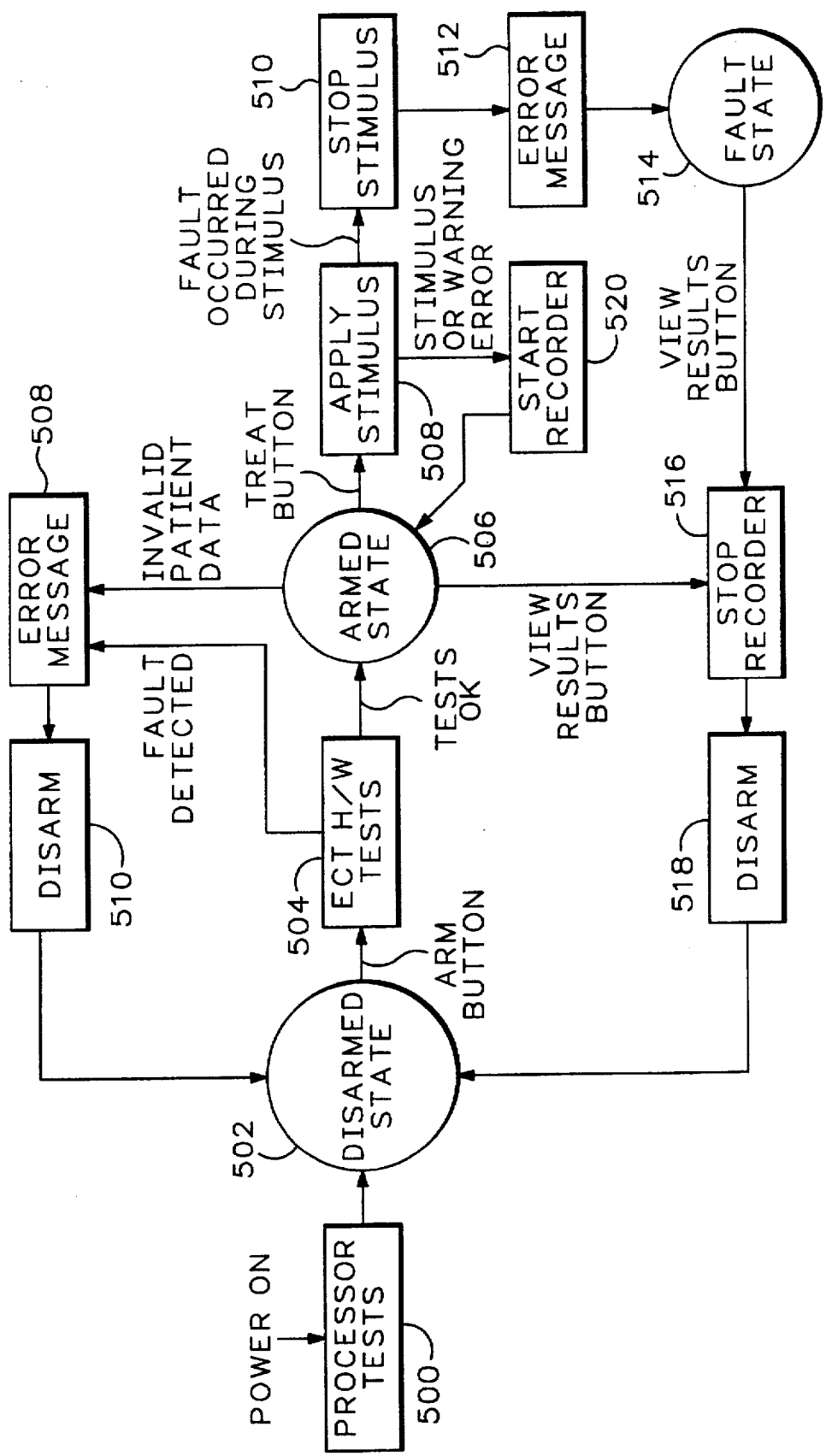
FIG. 14 is a flow chart of the operation of the system shown in FIG. 1.

Referring now to FIG. 14, a flow chart of the test sequencing of the system is shown. The test sequence begins in step 500 where the various processors perform their processor hardware start-up test sequences. This start-up sequence includes initializing ports and configuring them as either input or output ports. The general purpose registers are then tested by writing to and reading from all of the general purpose registers of the microprocessor. Certain processors include register banks and in those cases, each register bank is tested. In addition, some processors include special purpose registers. These registers can be tested in the same way as the general purpose registers, i.e., writing to and reading from those registers. Each processor includes a status register which includes a plurality of bits or fields that indicate the existence of a certain condition. These conditions are then forced by the microprocessor and then the corresponding status bit or field is tested. Each processor then executes a test of all internal and external memory. For the random access memory, the processor writes a predetermined pattern to each memory location and then reads it back. Usually, more than one write and read is required for each location to ensure that none of the memory cells are stuck in one state or the other. For read only memory, a cyclical redundancy check (CRC) is performed. Following these processor hardware start-up tests, each processor begins its normal program execution.

After the processor tests are completed in step 500, the system goes into a disarmed state 502. The disarmed state monitors the arm buttons (either on the touch screen or on the remote control unit) to detect the actuation of the arm button. If the arm button is actuated, the system executes a series of ECT hardware tests in step 504. If the arm button is not detected, the system performs a plurality of software tests. Each of these tests is discussed below.

In the disarmed state 502, there are a number of software and hardware safety tests that are performed. These tests are performed continuously while in this state. The first of these tests checks to see that there are valid trace data being received from the patient. If any of the patient monitoring signals saturate and remain there for a predetermined amount of time (e.g., one second), the system processor restores the trace by asserting the TRACE_RESTORE signal (FIG. 3). The safety processor also repetitively verifies that the hardware (HW), gated, ten-second, treatment duration timer is functional. The safety processor accomplishes this by allowing the hardware ten-second timer to expire and verifies that the TIMER EXPIRED signal is asserted. The safety processor itself includes a software (SW) ten-second treatment timer whose function is backed up by the hardware ten-second timer in the event that the software timer fails. The software verifies this hardware timer by allowing the hardware timer to expire and then verifies that the SW timer reads 10 seconds. If the software timer reaches 11 seconds without the HW timer expiring, the SW assumes a HW timer failure. If the software fails to receive the hardware timer interrupt at the completion of this test, an error condition exists. The safety processor also includes a general purpose timer that is used for a number of other functions. This timer is also checked while in the disarmed state in the same manner as the ten-second treatment timer.

The safety processor also checks the voltage level of the power supply voltages during this disarmed state. The safety processor samples the 33 volt, the -5 volt, the -12 volt and the 18 volt supply voltages and ensures that these voltages are within their specified tolerances. If not, the safety processor indicates an error condition exists. (Moreover, hardware voltage monitoring circuits will hold the system and safety processors in reset if the+5 volt or+12 supplies are out of their acceptable ranges.)

As described above, the system includes the ability to detect faults in the optional remote control unit. During this time, those tests are run to ensure the remote control unit is functioning properly.

If the arm button is actuated, the system will transition from the disarmed state and perform a plurality of ECT hardware tests in step 504. Each of these tests must be completed successfully in order to move to an arm state 506. If any failures occur, an error message is displayed in step 508, the system is disarmed in step 510 and the system returns to the disarmed state 502. A list of these ECT hardware tests is given below in Table 1 and a description of each follows.

TABLE 1

| ECT Hardware Test |
| --- |
| 1. 10,000 ohm static impedance test and calibration |
| 2. zero ohm static impedance test and calibration |
| 3. current calibration |
| 4. 300 ohm load delivery test |
| 5. zero ohm load delivery test |
| 6. energy limit test |
| 7. hardware watchdog test |
| 8. pulse width limit test |
| 9. frequency limit test |

Before executing any of the hardware self-tests, the system measures the patient impedance. If the patient impedance is outside an acceptable range (e.g., 100Ω–5 KΩ) the system generates an error message and terminates the arming process. Otherwise, the hardware self-tests are performed.

The first of these hardware self-tests is the 10,000 ohm static impedance test and calibration. During this test, the 10,000 ohm internal load is across the output circuit and the static impedance of this circuit is measured. The Z_PULSE produces an approximately 40 micro amp signal at 768 Hz through the load so that the impedance can be measured. The measured static impedance indication must be greater than a predetermined value in order for this test to pass. If the measured static impedance indication exceeds that value, the measured static impedance indication is saved as a 10,000 ohm calibration point.

The second test is similar to the first except that a zero ohm short is connected in the output circuit. This is accomplished by shorting the 10,000 ohm load with relay R2 (FIG. 11B). Once the zero load is switched in, the static impedance is again measured. In this case, however, the measured static impedance indication must be less than a predetermined minimum value. If the measured static impedance indication exceeds this minimum value, then an error condition exists. Otherwise, the measured static impedance indication is saved as a zero ohm calibration point. As part of this test, the output current is read. Because the 40 microamp current produced by the Z_PULSE is insufficient to be recognized by the safety processor, under normal conditions this will produce a current reading of zero. If there is a non-zero current value detected, however, the system saves this as a zero current calibration value, which can be used to compensate for any DC offset in the current measurement circuit.

Next, the safety processor initiates an energy delivery test into the internal 300 ohm load. This test verifies a successful delivery of a pre-treatment ECT pulse train to the internal 300 ohm load. As part of this test, the safety processor reads the energy counter 392 (FIG. 11B) and compares the detected energy with the expected delivered energy. If the measured energy is not within a predetermined tolerance of the estimated energy, then the test will fail. During this test, the dynamic impedance measurement is also verified. Because the pre-treatment ECT pulses are being delivered into a known load, the dynamic impedance should be approximately equal to 300 ohms. If the measured dynamic impedance is not within a predefined, acceptable range of this value, however, the test fails.

During the 300 ohm delivery test, the safety processor also verifies the software pulse train duration timer. During this test, the safety processor configures the system to generate a pulse train duration of a certain time, but then sets the software timer for less than that specified duration. Thus, the software should terminate the pulse train when the timer expires, if the software duration monitor is functioning properly. The safety processor then verifies that the treatment was in fact stopped. If not, the safety processor indicates that a error condition exists and disarms the machine.

As part of the zero ohm impedance testing calibration, the safety processor performs a zero ohm load delivery test. In this test, the system attempts to verify that the system properly terminates when delivering into an internal zero ohm load.

In another aspect of this test sequence, the system processor performs a plurality of energy limit tests. In these tests, the safety processor attempts to verify that the energy detector and monitor circuits work as designed. The safety processor first switches the clock 2 signal provided to the energy counters 392 (FIG. 11B) in order to accelerate the rate of counting transitions of signal JOULE_CLK. Signal DIVIDER_SELECT in FIG. 11B controls this acceleration, but acceleration is prevented during an actual ECT treatment. The processor then sets the number of pre-treatment pulses to be delivered equal to 10,000. The processor then initiates a pre-treatment ECT pulse train into the internal 300 ohm load and attempts to verify that a hardware shutdown (HW_SD) occurred at the level its software knows the hardware max energy limit select should be set. The safety processor verifies this by reading the ENERGY_MAX signal and the HW_SD signal. If not, the processor generates an error condition and disarms the circuit.

The safety processor itself also maintains a software energy limit counter as a backup to the hardware energy counter. Usually, the software energy limit counter is set above the hardware energy counter and, thus, trips only if the hardware counter fails. To test that this software energy limit counter is functioning properly, the software sets this internal software counter to a small value and again initiates a pre-treatment ECT pulse train. The processor then verifies that the pulse train was shut down by software after the appropriate amount of energy was delivered. The safety processor monitors the delivered energy by either counting the number of pulses or by monitoring the delivered voltage and current. The safety processor includes a plurality of A-to-D inputs for receiving these analog signals.

The system also includes a hardware watchdog test that is performed during step 504. In this test, the safety processor remains idle for a fixed period of time without retriggering the watchdog timer. After this fixed period of time, the safety processor verifies that the watchdog timer failed by reading the WD_FAILURE signal. The watchdog timer can then be reset by clocking the timer.

The system also monitors the pulse width of each ECT pulse to ensure that the pulse width is within a predetermined tolerance range of the specified pulse width. The safety processor generates the pulses by the use of two internal timers. The first timer sets the time between the leading and trailing edge of a pulse. The second timer specifies the time between the leading edge of a first pulse to the leading edge of a subsequent edge. Thus, the first timer sets the pulse width and the second timer the period or, alternatively, the frequency. The safety processor also monitors each edge of the resulting pulse and then verifies that the resulting pulse width is as specified by the timer values. In the preferred embodiment, each edge generates an interrupt and further traps the value of a system timer or time stamp. The interrupt service routine then reads this time stamp and compares it with the time stamp of the previous edge to determine the pulse width of the signal. The processor can also determine the period between pulses or the frequency by comparing the time stamps of corresponding edges in subsequent pulses.

During this test, the safety processor verifies that this software pulse width monitor is functioning properly. It does this by setting the timers to produce a pulse width of a certain time, yet checking for a different pulse width in the software monitoring routine. If functioning properly, this should produce an error condition responsive to which the safety processor will disable or terminate the ECT pulse train.

As described above, the hardware limits all pulses to a maximum pulse width of approximately 2.2 milliseconds. The software verifies that this limiting feature is functioning properly by setting the timer values to produce a pulse width in excess of this maximum allowable pulse width. The software then measures the pulse width of the delivered pulses and verifies that, in fact, they are being limited to the max 2.2 millisecond pulse width. If the pulses are not being so limited, the safety processor generates an error condition.

The system also performs a variety of frequency limit tests during this battery of hardware tests in step 504. There are two levels of frequency monitoring: software and hardware. In the software monitor, the frequency is measured on a pulse-by-pulse basis to determine whether or not the frequency is within a predetermined range of the specified frequency. On the hardware level, the hardware shuts down the ECT pulses if the frequency exceeds a predetermined maximum pulse frequency. Both of these are verified during the frequency limit test.

To test the software frequency monitor, the safety processor sets up a pulse train at a first frequency, but then assumes the frequency to be a different frequency value. The software processor then checks the frequency of each pulse by measuring the time between the corresponding edges of subsequent pulses (i.e., leading edge-to-leading edge or trailing edge-to-trailing edge. If the measured frequency falls outside of a specified range, as it should, the safety processor shuts down the pre-treatment ECT pulse train that is being delivered into the 300 ohm internal load. In this way, the safety processor can verify that its software frequency monitor is functioning properly.

The safety processor also verifies that the hardware frequency monitor is functioning properly. It accomplishes this by setting up a pulse train having a frequency in excess of the maximum allowable frequency. In the preferred embodiment, this maximum allowable frequency is approximately 220 Hz. The safety processor then configures the system to deliver this pulse train into the internal 300 ohm load and then verifies that the hardware frequency monitor disabled the delivery of the pulse train in response to this excessive frequency.

If all of these hardware self-tests are performed without error, the system enters the armed state 506. While in the armed state, the system continuously monitors patient impedance and checks to see that all patient monitoring leads are connected to the patient. If either of these two conditions are not met, the system disarms and displays an appropriate error message.

If, in the armed state 506, the system detects that the treatment button has been pressed, the system begins applying the actual ECT treatment pulse train in step 508. The parameters of the ECT treatment pulse train are those specified by the user via the front panel. These parameters include current, pulse width, frequency and duration. Unlike prior art ECT systems, the system according to the invention monitors each of these parameters during the treatment and terminates the treatment if any one of these parameters, as well as others, deviate from specified or predetermined values of these parameters. This avoids harm to the patient in the event that the failure occurs during an actual treatment.

The system performs several tests during treatment to detect any of these failure conditions. A list of these tests is given below in Table 2.

TABLE 2

Tests Performed During Treatment 1. maximum energy test
2. average current test
3. relay test
4. pulse width test
5. frequency test
6. voltage test
7. current test
8. pulse count test
9. duration test The first three tests listed above are actually performed upon entering the armed state, but prior to actual treatment.

The maximum energy test ensures that the energy level of the specified ECT treatment does not exceed the allowed regulatory energy limit. The energy level is calculated based on the parameter settings and an assumed standard patient impedance.

The average current test ensures that the average current of the requested ECT treatment does not exceed the maximum average current delivered by the system.

The relay control settings are also tested to ensure that the relays are properly configured. The system does this by reading the output signal level of DAC 414. This test is also performed any time the relay settings are changed.

The remaining tests are performed after the treatment has begun. Moreover, several of the tests (4–8) are performed on a pulse-by-pulse basis. The pulse width is measured by software by dating the time stamps that are trapped by the system processor upon detection of the trailing and leading edges of each pulse. The pulse width is then determined by simply subtracting the time stamp of the leading edge from that of the trailing edge. This detected pulse width is then compared with the specified pulse width, as set on the front panel, to determine whether the measured pulse width is within an acceptable tolerance of the specified pulse width. If the pulse width falls outside of that range, the safety processor terminates the treatment.

Similarly, the safety processor measures the frequency of the pulse train on a pulse-by-pulse or, rather, period-by-period basis. It does this by subtracting the time stamp of a leading edge of a pulse from a time stamp of a leading edge of the subsequent pulse to determine the period of that pulse. This detected period is then compared with the reciprocal of the specified frequency to determine whether the measured frequency is within an acceptable tolerance or range of the specified frequency. If not, the treatment is terminated.

The safety processor also monitors the voltage and current of each pulse and compares these measured values to those specified by the user. If this measured current is not within a predetermined range of the specified value, the processor terminates the treatment. The voltage on the other hand must be less than a predetermined maximum voltage. As described above, the safety processor included one or more A-to-D inputs that are used to sample the signal levels of these signals (e.g., DELIV__I, DELIV__V, etc.).

The safety processor also maintains a Count of the number of delivered pulses and the number of measured pulses to ensure that the safety processor is not falling behind and is, in fact, processing each pulse as it occurs. If the safety processor falls behind, i.e., delivered pulse count is greater than the measured pulse count, the safety processor assumes that it has become overloaded and therefore terminates the treatment as well.

During the ECT treatment, the software keeps retriggering the watchdog timer. If this watchdog times out, the ECT hardware terminates the treatment.

Finally, if the operator prematurely terminates the treatment, the ECT hardware terminates the treatment and notifies the safety processor.

If any fault or error occurs during the stimulus, the system in addition to terminating the stimulus, generates an error message in step 512, which logs the source of the faults. The system then enters a fault state 514 and waits there until the view results button is pushed on the front panel. The view results button causes the recorder to stop recording patient monitoring waveforms in 516 and, further, displays the error message to the user. Following this, the system is disarmed in step 518 and returns to the disarm state 502.

B. OPTICAL MOTION SENSOR

In another aspect of the invention, a non-invasive, optical sensor is used to detect seizure-induced patient motion. As is known in the art of ECT, the primary benefit of ECT is produced by induced seizures. It is therefore important for the clinician to monitor the level of induced seizure of the patient.

Shown in FIG. 15 is the preferred method of monitoring a patient seizure activity. In FIG. 15, an optical detector 528 is mounted on a patient's digit 530 about the knuckle. The knuckle area is chosen because the effects of blood flow on the measurement is minimized. Furthermore, the relative magnitude of the patient's heartbeat signal detected is minimized when the detector is mounted on the "nail" side of the knuckle, and the signal proportional to knuckle flexing maximized.

The optical detector includes a light-emitting diode 532 and an optical detector such as a photoresistor 534. The light-emitting diode 532 emits light that is reflected off of the knuckle and detected by photoresistor 534. The photoresistor 534 then produces a patient monitoring signal OMS that is proportional to the intensity of the light received thereby. A 3.6 volt supply voltage (3.6 V) is applied to the LED 532 to provide power thereto. An ECT-induced seizure will be manifest by twitching flexions of the knuckle. This changes the amount of light received by the detector 534 responsive to the expansion and contraction of the muscle under the surface. Thus, the optical detector 528 can effectively be used to monitor ECT-induced seizure activity.

Typically, a muscle relaxant is applied to the patient prior to an ECT treatment. In order for the optical motion sensor to work properly, the clinician must prevent the muscle relaxant from affecting the digit on which the sensor is located. One way to accomplish this is to constrict the user's appendage to which the digit 530 is connected so as to limit the blood flow, and therefore the muscle relaxant, to the digit. A simple blood pressure cuff can be used to accomplish this, when inflated to a pressure above the patient's systolic blood pressure.

Having described and illustrated the principles of the invention in a preferred embodiment thereof, it should be apparent that the invention can be modified in arrangement and detail without departing from such principles. I claim all modifications and variation coming within the spirit and scope of the following claims.

We claim:

1. A method of ensuring the safety of a patient during electro-convulsive therapy (ECT) by automatic self test and operation of ECT apparatus, the method comprising:

applying a pre-treatment pulse train to a dummy load including a plurality of individual pre-treatment pulses, each pre-treatment pulse having pulse parameters that define the pulse, the pulse parameters defining a set of pulse train parameters;

measuring a pulse train parameter of the pre-treatment pulse train across the dummy load; and applying a treatment pulse train to the patient only if the measured pulse train parameter satisfies a predetermined criteria; and disabling the apparatus from applying the treatment pulse train to the patient if the measured pulse train parameter fails the predetermined criteria.

2. A method of ensuring the safety of a patient during electro-convulsive therapy (ECT) according to claim 1 wherein the step of measuring a pulse train parameter includes the step of measuring a pulse width of a pre-treatment pulse.

3. A method of ensuring the safety of a patient during electro-convulsive therapy (ECT) according to claim 1 wherein the step of measuring a pulse train parameter includes the step of measuring a frequency of the pre-treatment pulse train.

4. A method of ensuring the safety of a patient during electro-convulsive therapy (ECT) according to claim 1 wherein the step of measuring a pulse train parameter includes the step of measuring a duration of the pre-treatment pulse train.

5. A method of ensuring the safety of a patient during electro-convulsive therapy (ECT) according to claim 1 wherein the step of measuring a pulse train parameter includes the step of measuring a power of the pre-treatment pulses.

6. A method of ensuring the safety of a patient during electro-convulsive therapy (ECT) according to claim 5 wherein the step of measuring a power of pre-treatment pulses includes:

measuring a voltage of a pre-treatment pulse;

measuring a current of the pre-treatment pulse; and multiplying the measured current and the measured voltage to produce the measured power.

7. A method of ensuring the safety of a patient during electro-convulsive therapy (ECT) according to claim 6 wherein the step of measuring a pulse train parameter includes the step of measuring an energy of the pre-treatment pulse train.

8. A method of ensuring the safety of a patient during electro-convulsive therapy (ECT) according to claim 7 wherein the step of measuring an energy of the pre-treatment pulse train includes integrating the measured power.

9. A method of ensuring the safety of a patient during electro-convulsive therapy (ECT) according to claim 8 wherein the step of integrating the measured power includes:

converting the measured power to a power signal having a frequency proportional to the measured power; and incrementing a counter by the power signal to produce a count signal that is proportional to the measured energy.

10. A method of ensuring the safety of a patient during electro-convulsive therapy (ECT) according to claim 1 further comprising:

applying a train of treatment pulses to a patient;

measuring a pulse train parameter of the treatment pulse train applied to the patient; and terminating the treatment pulse train if the measured pulse train parameter of the treatment pulse train fails to satisfy a predetermined criteria.

11. A method of ensuring the safety of a patient during electro-convulsive therapy (ECT) according to claim 10 wherein the step of measuring a pulse train parameter includes the step of measuring a pulse width of the treatment pulses.

12. A method according to claim 10 in which each treatment pulse has a pulse width, the elapsed time of the pulse train defines a pulse train duration, and the time between adjacent pulses defines a frequency of the treatment pulse train;

the measuring step includes a pulse width detection step that measures the pulse width of each applied ECT treatment pulse; and the terminating step includes a pulse width monitoring step responsive to the pulse width to cease applying the treatment pulses to the patient if a measured pulse width exceeds a predetermined maximum pulse width.

13. A method according to claim 10 in which each treatment pulse has a pulse width, the elapsed time of the pulse train defines a pulse train duration, and the time between adjacent pulses defines a frequency of the treatment pulse train;

the measuring step includes a pulse train duration detection step that measures the duration of the applied ECT treatment pulse train; and the terminating step includes a pulse train duration monitoring step responsive to the pulse train duration to cease applying the treatment pulses to the patient if the measured pulse train duration exceeds a maximum pulse train duration.

14. A method according to claim 10 in which each treatment pulse has a pulse width, the elapsed time of the pulse train defines a pulse train duration, and the time between adjacent pulses defines a frequency of the treatment pulse train;

the measuring step includes a pulse train energy detection step that measures the energy in the applied ECT treatment pulse train; and the terminating step includes a pulse train energy monitoring step responsive to the pulse train energy to cease applying the treatment pulses to the patient if the measured pulse train energy exceeds a predetermined limit.

15. A method according claim 14 wherein the step of pulse train energy detection includes:

a power detection step that generates a power signal having a signal level corresponding to the power of each applied ECT treatment pulse; and an integration step receiving the power signal and generating an energy signal corresponding to the level of energy of the applied ECT treatment pulse train.

\* \* \* \* \*

UNITED STATES PATENT AND TRADEMARK OFFICE
CERTIFICATE OF CORRECTION

PATENT NO. : 5,755,744
DATED : May 26, 1998
INVENTOR(S) : Shaw et al.

It is certified that error appears in the above-identified patent and that said Letters Patent is hereby corrected as shown below:

Abstract, line 14, "detect plurality" should read --detect the plurality--
Column 1, line 38, "pentylenetetrazol induced" should read --pentylenetetrazol-induced--
Column 15, line51, "Δ-=xdiffx[i Bxcos (phase)-Axsin (phase)]" should read --$\Delta$ -= $\beta$ x diff x [B x cos (phase) - A x sin (phase)--
Column 18, line 32, "to and front" should read --to and from--
Column 19, line 52, "in a non-retriggerable" should read --in a non-retriggerable--
Column 19, line 61, "PULSE$_{13}$IN" should read --PULSE_IN--
Column 20, line 25, "shown) one" should read --shown) -- one--
Column 22, line 53, "RC$_{13}$SENSE" should read --RC_SENSE--
Column 24, line 22, "WD$_{13}$CLK" should read --WD_CLK--

Signed and Sealed this

Sixteenth Day of May, 2000

*Attest:*

Q. TODD DICKINSON

*Attesting Officer*  *Director of Patents and Trademarks*